United States Patent
Wacker et al.

(10) Patent No.: US 10,973,901 B2
(45) Date of Patent: Apr. 13, 2021

(54) **PRODUCTION OF RECOMBINANT VACCINE IN *E. COLI* BY ENZYMATIC CONJUGATION**

(71) Applicant: GLAXOSMITHKLINE BIOLOGICALS SA, Rixensart (BE)

(72) Inventors: Michael Wacker, Unterengstringen (CH); Michael Kowarik, Zurich (CH); Michael Wetter, Zurich (CH); Amirreza Faridmoayer, Zurich (CH)

(73) Assignee: GlaxoSmithKline Biologicals SA, Rixensart (BE)

(*) Notice: Subject to any disclaimer, the term of this patent is extended or adjusted under 35 U.S.C. 154(b) by 0 days.

(21) Appl. No.: 16/034,906

(22) Filed: Jul. 13, 2018

(65) Prior Publication Data

US 2019/0076517 A1 Mar. 14, 2019

Related U.S. Application Data

(62) Division of application No. 14/440,311, filed as application No. PCT/EP2013/073266 on Nov. 7, 2013, now abandoned.

(60) Provisional application No. 61/723,408, filed on Nov. 7, 2012.

(51) Int. Cl.
| | |
|---|---|
| *A61K 39/085* | (2006.01) |
| *A61K 39/09* | (2006.01) |
| *C12N 15/70* | (2006.01) |
| *C12P 21/00* | (2006.01) |
| *A61K 39/00* | (2006.01) |

(52) U.S. Cl.
CPC .......... *A61K 39/092* (2013.01); *C12N 15/70* (2013.01); *C12P 21/005* (2013.01); *A61K 2039/523* (2013.01); *A61K 2039/55566* (2013.01); *A61K 2039/6037* (2013.01); *Y02A 50/401* (2018.01); *Y02A 50/41* (2018.01); *Y02A 50/412* (2018.01); *Y02A 50/47* (2018.01); *Y02A 50/478* (2018.01)

(58) Field of Classification Search
None
See application file for complete search history.

(56) References Cited

U.S. PATENT DOCUMENTS

| 5,948,900 A | 9/1999 | Yother et al. |
| 2005/0281841 A1 | 12/2005 | Kopecko et al. |

FOREIGN PATENT DOCUMENTS

| JP | 2002503705 A | 2/2002 |
| JP | 2012521423 A | 9/2012 |
| WO | 1999042130 A1 | 8/1999 |
| WO | 2010110931 A2 | 9/2010 |
| WO | 2014057109 A1 | 4/2014 |

OTHER PUBLICATIONS

Lehane et al (J. Biochem. 2005. 389:137-143).*
Wang et al (Microbio. 2007, 153: 2159-2167).*
Stagg et al (J. Bacteriol. Nov. 2009, p. 6612-6617).*
Ada et al., "Carbohydrate-protein conjugate vaccines", Clin Microbol Infect, Feb. 2003, vol. 9, No. 2 pp. 79-85.
Bayer, M et al., "Poly Saccharide Capsule of *Escherichia-coli* Microscope Study of its size Structure and Sites of Synthesis", Journal of Bacteriology, 1977, vol. 130, No. 2, pp. 911-936.
Bentley et al., "Genetic Analysis of the Capsular Biosynthetic Locus from All 90 Pneumococcal Serotypes". PLOS Genetics, Mar. 2006, vol. 2(3), pp. 0262-0269.
Dempski et al., Heterologous expression and biophysical characterization of soluble oligosaccharyl transferase subunits, 2004 Archives of Bioch. & Biophysics 431:63-70.
Feldman et al., Engineering N-linked protein glycosylation with diverse O antigen lipopolysaccharide structures in *Esherichia coli*, Proc Natl Acad Sci USA., 2005, vol. 102, No. 8, pp. 3016-3021.
Gambillaraet al, Clinical Microbiology and Infection, May 2011, vol. 17, Supp. Suppl. 4, pp. S408. Abstract No. P1446.
Ihssen et al., "Production of glycoprotein vaccines in *Escherichia coli*", Microbiobial Cell Factories, 2010, 9(61), pp. 1-13.
Ihssen et al., Structural insights from random mutagenesis of Campylobacter jejuni oligosaccharyltransferase PgIB, BMC Biotechnology, 2012, 12(67), pp. 1-13.
Intellectual Property Office of Singapore, Written Opinion for Application No. 11201503308X dated Dec. 12, 2016; 7 pages.
Koji Hayashi et al., "Highly accurate genome sequences of *Escherichia coli* K-12 strains MG1655 and W3110," Molecular Systems Biology, vol. 2, Feb. 21, 2006 (Feb. 21, 2006), XP055355138, DOI: 10.1038/MSB4100049.
Lee, C-J et al., "Immunogenicity in Mice of Pneumococcal Glycoconjugate Vaccines Using Pneumonoccal Protein Carriers", Vaccine, Apr. 2001, vol. 19, No. 23-24, pp. 3216-3225.
Lehane, Adele M. et al., Bacteriophage-encoded glucosyltransferase GtrII of Shigella flexneri: membrane topology and identification of critical residues, The Biochemical Journal, Jul. 1, 2005 (Jul. 1, 2005), pp. 137-143, XP055520770, England, DOI: 10.1042/BJ20050102 Retrieved from the Internet: URL:https://www.ncbi.nlm.nih.gov/pmc/artic les/PMC1184546/pdf/bj3890137.pdf.
Lin et al., "Sequence Analysis and Molecular Characterization of Genes Required for the Biosynthesis of Type 1 Capsular Polysaccharide in *Staphylococcus aureus*", Journal of Bacteriology, vol. 176, No. 22, Nov. 1994, pp. 7005-7016.
Lizak et al., X-ray structure of bacterial oligosaccharyltransferase, 2011 Nature 474: 350-355.
Munoz et al.,"Molecular organization of the genes required for the synsthesis of type 1 capsular polysaccharide of *Streptococcus pneumonia*: formation of binary encapsulated pneumococci and identification of cryptic dTDP-rhamnose biosynthesis genes.", Molecular Microbiology, 1997, vol. 25 No. 1, pp. 79-92.

(Continued)

*Primary Examiner* — Jennifer E Graser
(74) *Attorney, Agent, or Firm* — Dana L. Broughton

(57) ABSTRACT

Provided herein are prokaryotic cells proficient to produce glycoconjugates in vivo, as well as methods for generating these cell and methods of using these cells to produce glycoconjugates. The compositions of the mentioned glycoconjugates as well as their different uses are also included.

16 Claims, 25 Drawing Sheets

(56) References Cited

OTHER PUBLICATIONS

Sau et al., "The *Staphylococcus aureus* allelic genetic loci for serotype 5 and 8 capsule expression contain the type-specific genes flanked by common genes", Microbiology, 1997. vol. 143(7), pp. 2395-2405.
Sutherland, Ian, et al.; "Microbial Polysaccharides from Gram-negative bacteria", International Dairy Journal, 2001, vol. 11, No. 9, pp. 663-674.
Toniolo, et al., "*Streptococcus agalactiae* capsule polymer length and attachment is determined by the proteins CpsABCD" J. Biol. Chem.; Feb. 9, 2015; pp. 1-27.
Vario et al., Evolution of the Capsular Regulatory Genes in *Streptococcus pneumoniae*, 2009 J. Inf. Dis. 200:1144-1151.
Wacker, et al., "N-Linked slycosylation in Campylobacter jejuni and its Functional Transfer into *E. coli*" Science, American Association for the Advancement of Science, Nov. 29, 2002, vol. 298, pp. 1790-1793.
Whitfield, Chris, "Biosynthesis and assembly of capsular polysaccharides in *Escherichia coli*", Annual Review of Biochemistry, Palto Alto, CA, US, vol. 75, Jan. 1, 2006 (Jan. 1, 2006), pp. 39-68, XP002470743, ISSN: 0066-4154, DOI: 10.1146/ANNUREV.BIOCHEM.75.103004.142545.
Guan,et al., "Functional analysis of the O antigen glucosylation gene cluster of Shigella flexneri bacteriophage SfX," 1999, Microbiology, vol. 145, pp. 1263-1273.

\* cited by examiner

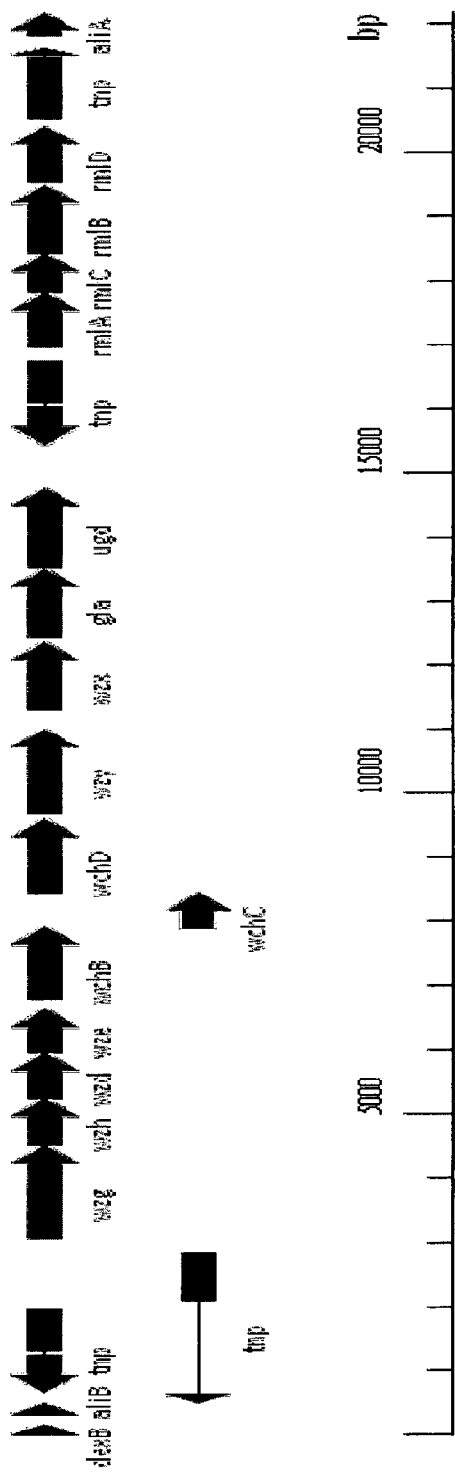
Fig. 2
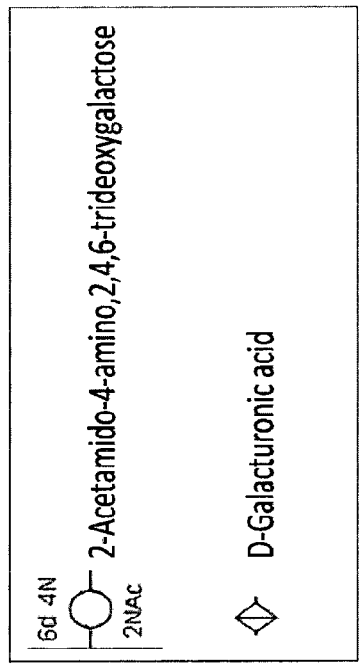
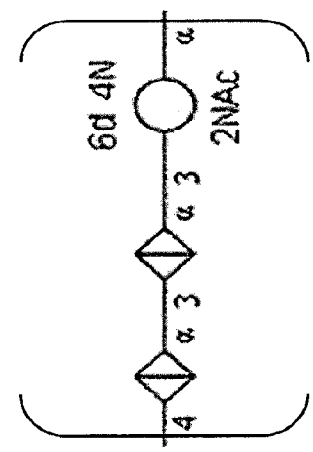
Fig. 3

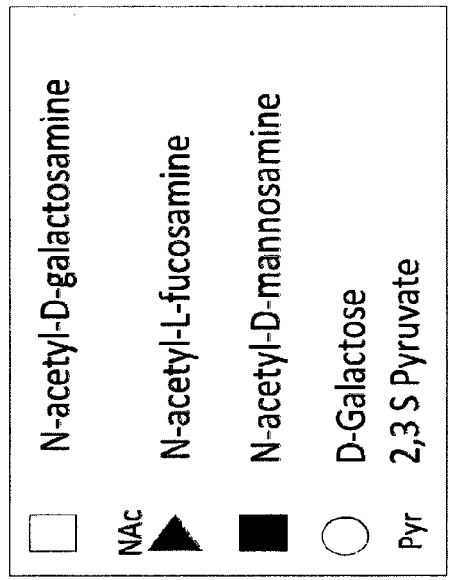
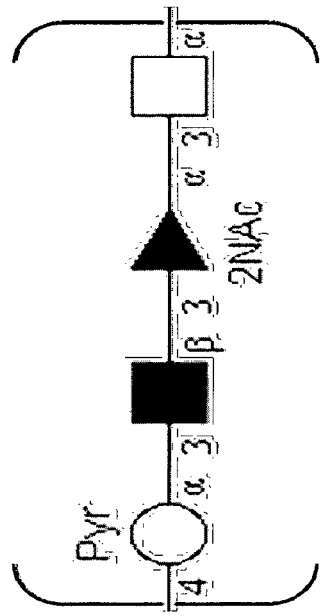
Fig. 10
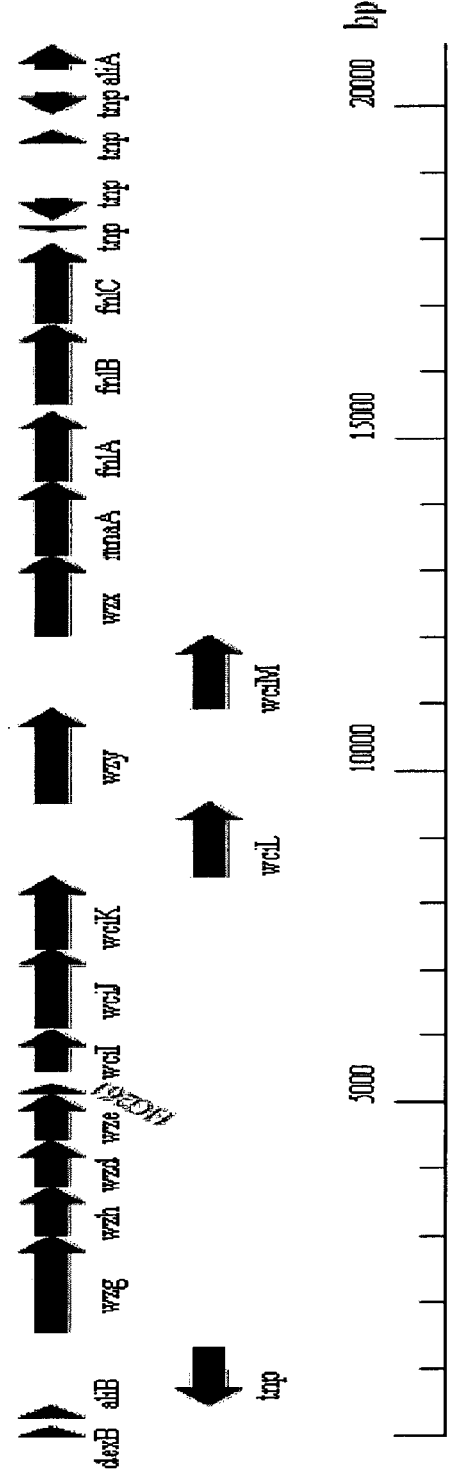
Fig. 11

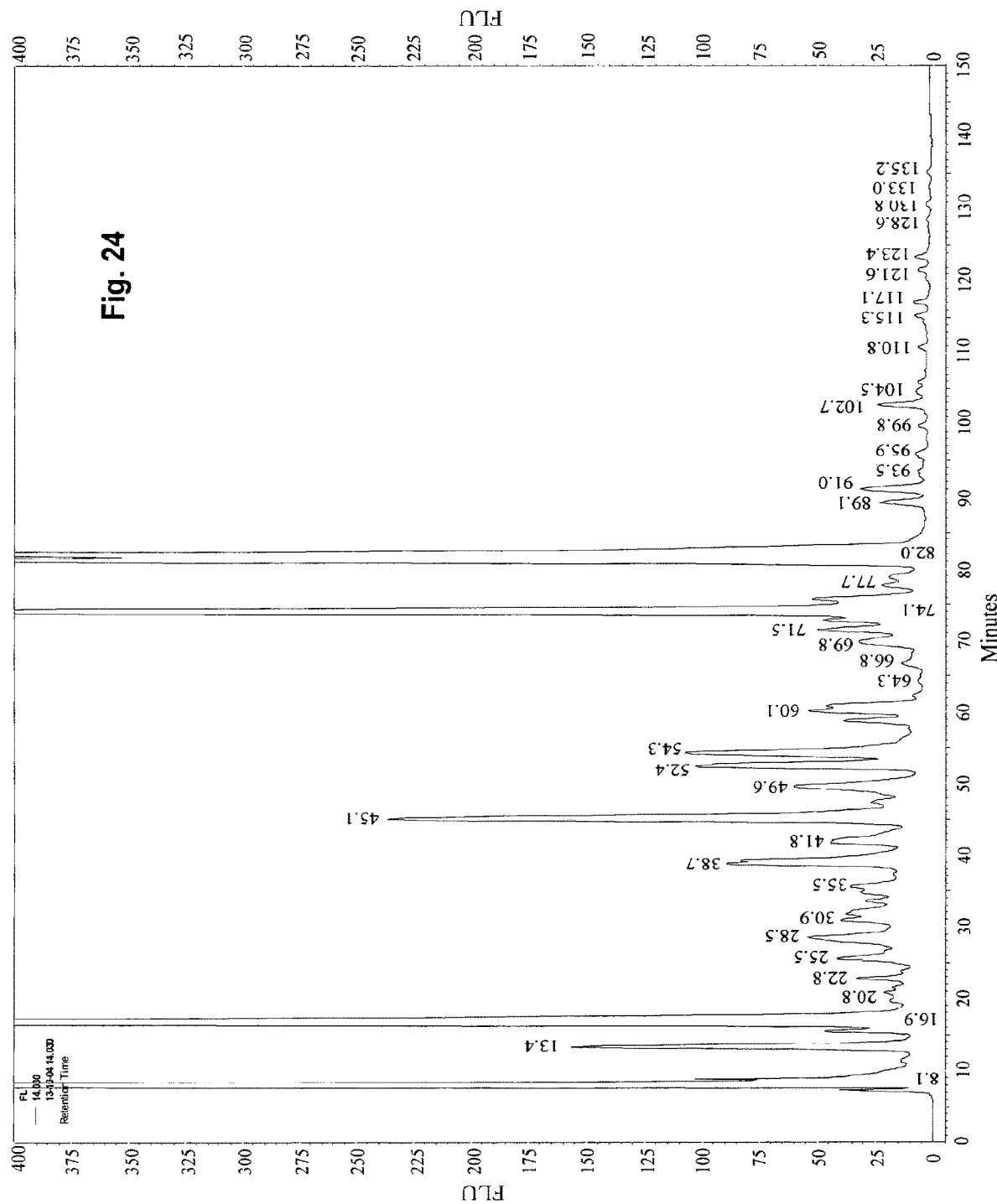

PRODUCTION OF RECOMBINANT VACCINE IN *E. COLI* BY ENZYMATIC CONJUGATION

1—INTRODUCTION

Provided herein are prokaryotic cells proficient to produce glycoconjugates in vivo, as well as methods for generating these cell and methods of using these cells to produce glycoconjugates. The compositions of the mentioned glycoconjugates as well as their different uses are also included.

2—BACKGROUND

Glycosylation is a process by which carbohydrate molecules or sugars (monosaccharides, disaccharides, oligosaccharides, or polysaccharides) are attached to the side chains of different amino acids residues in a protein or polypeptide to generate a glycoprotein.

Glycoproteins are involved in several processes such as, cellular interaction and cell signaling; they participate in protein folding, oligomerization, stability, quality control, sorting and transport of secretory and membrane proteins. Protein glycosylation has a profoundly favorable influence on the antigenicity, the stability and the half-life of a protein.

There are different sort of glycoproteins depending of the type of linkage between the carbohydrate molecules and the amino acid residue in the protein carrier.

N-linked protein glycosylation—the addition of carbohydrate molecules to an asparagine residue in the polypeptide chain of the target protein—is the most common type of post-translational modification occurring in the endoplasmic reticulum of eukaryotic organisms. The process is accomplished by the enzymatic oligosaccharyltransferase complex (OST) responsible for the transfer of a preassembled oligosaccharide from a lipid carrier (dolichol phosphate) to an asparagine residue of a nascent protein within the conserved sequence Asn-X-Ser/Thr (where X is any amino acid except proline) in the Endoplamic reticulum. The saccharide chain is then subject to other modifications in the Golgi apparatus. The N-linked glycosylation process occurs in eukaryotes and widely in archaea, but very rarely in bacteria (see below).

O-linked glycosylation is a form of glycosylation that occurs in eukaryotes, archaea and bacteria. It consists in the attachment of a sugar molecule to an oxygen atom in an amino acid residue in the protein target.

It has been shown that a bacterium, the food-borne pathogen *Campylobacter jejuni*, can also N-glycosylate its proteins (Wacker et al., *Science*. 2002; 298(5599):1790-3) due to the fact that it possesses its own glycosylation machinery. The machinery responsible of this reaction is encoded by a cluster called pgl (for protein glycosylation).

The *C. jejuni* glycosylation machinery can be transferred to *E. coli* to allow for the glycosylation of recombinant proteins expressed by the *E. coli* cells. Previous studies have demonstrated how to generate *E. coli* strains that can perform N-glycosylation (see, e.g., Wacker et al., *Science*. 2002; 298 (5599):1790-3; Nita-Lazar et al., *Glycobiology*. 2005; 15(4):361-7; Feldman et al., *Proc Natl Acad Sci USA*. 2005; 102(8):3016-21; Kowarik et al., *EMBO J*. 2006; 25(9):1957-66; Wacker et al., *Proc Natl Acad Sci USA*. 2006; 103(18):7088-93; International Patent Application Publication Nos. WO2003/074687, WO2006/119987, WO 2009/104074, and WO/2011/06261, and WO2011/138361).

Bacteria can be divided in two groups, Gram-positive and Gram-negative, depending if they have either a single or double sheath cell membrane that is often surrounded by capsular polysaccharides. Examples for such bacteria include *Streptococcus* ssp., *Pseudomonas* ssp., *Neisseria* ssp., *Salmonella* ssp., *Escherichia* ssp., *Staphylococcus* ssp., *Campylobacter* ssp., etc. One of the medically and commercially most relevant infectious agent is *Streptococcus pneumoniae*, a Gram-positive pathogen.

*S. pneumoniae* is the major cause of both mild and severe infections worldwide. The primary clinical syndromes associated with pneumococcal infections are pneumonia, meningitis, bloodstream infections and acute otitis media, with pneumonia being the most important of these in terms of morbidity and mortality. Infections caused by *S. pneumoniae* are responsible for substantial disease burden particularly in the very young and in the elderly (Isaacman D J, M. E., Reinert R R. 2010. Burden of invasive pneumococcal disease and serotype distribution among *Streptococcus pneumoniae* isolates in young children in Europe: impact of the 7-valent pneumococcal conjugate vaccine and considerations for future conjugate vaccines. *Int J Infect Dis*. 14:197-209).

Pneumococci are grouped into several serotypes (~93) on the basis of their chemically and serologically distinct capsular polysaccharides. Certain serotypes are more abundant than others, to be associated with clinically apparent infections, to cause severe invasive infections and to acquire resistance to one or more classes of antibacterial agents (Rueda, A. M. M., MSc; Serpa, José A. MD; Matloobi, Mahsa MD; Mushtaq, Mahwish MD; Musher, Daniel M. MD. 2010. The spectrum of invasive pneumococcal disease at an adult tertiary care hospital in the early 21st century. *Medicine* (Baltimore) 89:331-336). Distinct serotypes of *S. pneumoniae* have been identified based on structural differences in the polysaccharide capsule. According to previous analyses approximately 10 or 11 serotypes account for over 70% of invasive pediatric infections in all regions of the world (Hausdorff W P, Bryant J, Paradiso P R, Siber G R: Which pneumococcal serogroups cause the most invasive disease: implications for conjugate vaccine formulation and use, part I. Clinical infectious diseases: an official publication of the *Infectious Diseases Society of America* 2000, 30(1):100-121). The distribution of serotypes causing disease varies by age, disease syndrome, disease severity, geographic region, and over time. Pneumococci that are resistant to penicillin, erythromycin, co-trimoxazole or multiple drugs are common in many regions (Evolving trends in *Streptococcus pneumoniae* resistance: implications for therapy of community-acquired bacterial pneumonia. Jones R N, Jacobs M R, Sader H S. *Int J Antimicrob Agents*. 2010 September; 36(3):197-204)

The pneumococcal capsule is one of the main bacterial virulence factors and has been successfully used as antigen in various vaccines. Antibodies against the capsular polysaccharide have been shown to be protective against pneumococcal infection (Musher D M PH, Watson D A, Baughn R E: Antibody to capsular polysaccharide of *Streptococcus pneumoniae* at the time of hospital admission for Pneumococcal pneumonia. *J Infect Dis* 2000, 182(1):158-167, Isaacman D J M E, Reinert R R: Burden of invasive pneumococcal disease and serotype distribution among *Streptococcus pneumoniae* isolates in young children in Europe: impact of the 7-valent pneumococcal conjugate vaccine and considerations for future conjugate vaccines. *Int J Infect Dis* 2010, 14(3):197-209)

The pathways of pneumococcal capsular polysaccharides (CPS) synthesis differ depending on the serotype (~93). With the exception of types 3 and 37, which are synthesized by the synthase pathway (Bentley S D, Aanensen D M, Mavroidi A, Saunders D, Rabbinowitsch E, Collins M, Donohoe K, Harris D, Murphy L, Quail M A et al: Genetic analysis of the capsular biosynthetic locus from all 90 pneumococcal serotypes. *PLoS genetics* 2006, 2(3):e31) pneumococcal CPSs are generally synthesized by the O-Antigen-Flippase (Wzx)/Polymerase (Wzy)-dependent pathway (FIG. 1).

CPSs are assembled from common precursors (e.g. nucleotide activated monosaccharides) on carrier lipids by a step-wise approach. First, the repeat unit is assembled on the carrier at the cytoplasmic side of the membrane by different glycosyltransferases. The lipid-linked oligosaccharide is then flipped to outer side of the membrane where the repeating units are polymerized. The complete CPS is released from the carrier lipid and exported to the surface.

Bacterial polysaccharides can elicit a long-lasting immune response in humans if they are coupled to a protein carrier that contains T-cell epitopes. This concept was elaborated almost 100 years ago (Avery, O. T., and W. F. Goebel, 1929. Chemo-immunological studies on conjugated carbohydrate-proteins Immunological specificity of synthetic sugar-proteins. *J. Exp. Med.* 50:521-533), and proven later for the polysaccharide of *Haemophilus influenza* type B (HIB) coupled to the protein carrier diphtheria toxin (Anderson, P. 1983. Antibody responses to *Haemophilus influenzae* type b and diphtheria toxin induced by conjugates of oligosaccharides of the type b capsule with the nontoxic protein CRM197. *Infect Immun* 39:233-8; Schneerson, R., O. Barrera, A. Sutton, and J. B. Robbins. 1980. Preparation, characterization, and immunogenicity of *Haemophilus influenzae* type b polysaccharide-protein conjugates. *J Exp Med* 152:361-76). This glycoconjugate was also the first conjugated vaccine to be licensed in the USA in 1987 and introduced into the US infant immunization schedule shortly thereafter. Besides HIB, conjugated vaccines have been successfully developed against the encapsulated human pathogens *Neisseria meningitidis* and *S. pneumoniae*. Routine use of these vaccines has resulted in decreased nasopharyngeal colonization, as well as infection. Currently ~25% of the global vaccine market comprises conjugated vaccines.

Conjugate vaccines have been successfully used to protect against bacterial infections. The conjugation of an antigenic polysaccharide to a protein carrier is required for protective memory response, as polysaccharides are T-cell independent antigens. Polysaccharides have been conjugated to protein carriers by different chemical methods, using activation reactive groups in the polysaccharide as well as the protein carrier (Pawlowski, A., G. Kallenius, and S. B. Svenson. 2000. Preparation of pneumococcal capsular polysaccharide-protein conjugates vaccines utilizing new fragmentation and conjugation technologies. *Vaccine* 18:1873-1885; Robbins, J. B., J. Kubler-Kielb, E. Vinogradov, C. Mocca, V. Pozsgay, J. Shiloach, and R. Schneerson. 2009. Synthesis, characterization, and immunogenicity in mice of *Shigella sonnei* O-specific oligosaccharide-core-protein conjugates. *Proc Natl Acad Sci USA* 106:7974-7978).

Conjugate vaccines can be administered to children to protect them against bacterial infections and can provide a long lasting immune response to adults. Constructs of the invention have been found to generate an IgG response in animals. It is believed that the polysaccharide (i.e. sugar residue) triggers a short-term immune response that is sugar-specific. Indeed, the human immune system generates a strong response to specific polysaccharide surface structures of bacteria, such as O-antigens and capsular polysaccharides. However, as the immune response to polysaccharides is IgM dependent, the immune system develops no memory. The protein carrier that carries the polysaccharide, however, triggers an IgG response that is T-cell dependent and that provides long lasting protection since the immune system develops memory. For this reason, it is advantageous to develop a vaccine as a protein carrier-polysaccharide conjugate.

The inability of pure pneumococcal polysaccharide vaccines to induce a protective immune response for important serotypes in young children precludes their consideration for infant immunization.

To date, vaccines against pneumococcal disease are synthesized in vitro by a well-established chemical conjugation technology. Antigenic capsular polysaccharides are extracted from pathogenic organisms, purified, chemically activated and conjugated to a suitable protein carrier. Currently, there are different protein carriers used to produce the glycoconjugates e.g. CRM197 (diphtheria toxoid), tetanus toxoid, and *Hemophilus influenzae* protein D.

A 7-valent pneumococcal conjugate vaccine (PCV7) has been licensed several years ago and it has been recommended for use in developing countries with high disease burden by WHO's Strategic Advisory Group of Experts (SAGE) (*Vaccine* 2012 Jul. 6; 30(32):4717-8. Epub 2012 May 20. Pneumococcal vaccines WHO position paper—2012-recommendations. WHO Publication). A 10-valent (PCV10) and a 13-valent (PCV13) conjugate vaccine have been licensed as well in various countries. Additional conjugate vaccines are at different stages of development (Jiang S M, Wang L and Reeves P R: Molecular characterization of *Streptococcus pneumoniae* type 4, 6B, 8, and 18C capsular polysaccharide gene clusters. *Infect Immun* 2001, 69(3): 1244-1255).

Several problems have been identified in the context of the manufacturing of chemical conjugate vaccines. Chemical treatment of polysaccharides for conjugation has been shown to impair the natural conformation of the polysaccharide influencing the quality of the antigens, consequently, affecting the antigenicity and immunogenicity of the final product (Impact of the conjugation method on the immunogenicity of *Streptococcus pneumoniae* serotype 19F polysaccharide in conjugate vaccines (Poolman J, Frasch C, Nurkka A, Käyhty H, Biemans R, Schuerman L. *Clin Vaccine Immunol.* 2011 February; 18(2):327-36. Epub 2010 Dec. 1).

3—SUMMARY OF THE INVENTION

This invention describes a novel method to produce glycoconjugate vaccines that contain polysaccharides from pneumococcal cells. This innovative pneumococcal vaccine is based on the discovery that regulatory genes involved in oligo—or polysaccharide biosynthesis of a Gram-positive bacteria can be used to efficiently synthetize oligo—and polysaccharides in a Gram-negative host strain, and that the oligo—or polysaccharide produced in this way can be used to make a glycoconjugate vaccine in the Gram-negative host cells. Further novel and unexpected features of the invention include without limitation the embodiments set forth below.

The presented invention describes an original procedure for the production of pneumococcal polysaccharide based conjugate vaccines. The procedure is based on various steps:

i) Recombinant production of pneumococcal polysaccharides as undecaprenyl-pyrophosphate (Und-PP) linked O antigen like polysaccharides in *E. coli* using regulatory genes that enhance production efficiency of polysaccharides.

ii) Development of a suitable production strain by deleting specific functions of the initial strain to make the polysaccharide production more efficient.

iii) Design of suitable DNA constructs that allow the efficient, recombinant synthesis of pneumococcal polysaccharides in E. coli.

iv) A method for efficient conjugation in vivo of polysaccharides to an acceptor protein by an oligosaccharyltransferase.

4—BRIEF DESCRIPTION OF THE FIGURES

FIG. 2 Shows the genetic organization related to CPS 1 biosynthesis. CPS1 genetic organization, wzg to rmlD are genes that are involved in biosynthesis of capsular polysaccharide.

FIG. 3 Illustrates a CPS 1 subunit. Schematic diagram of a CPS1 subunit.

Figure 6:
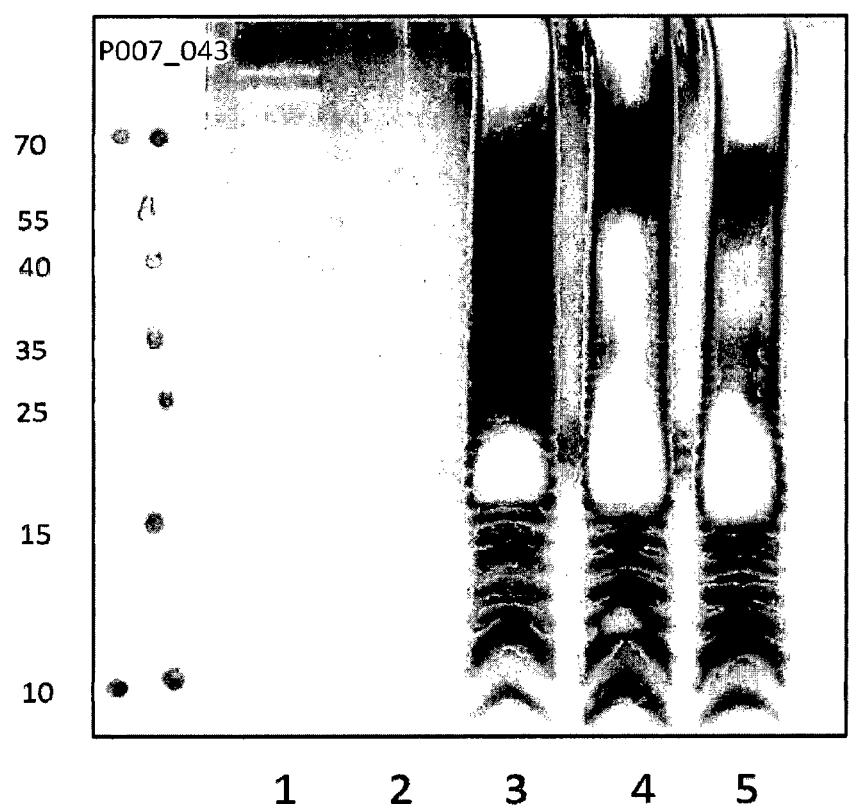

FIG. 6 displays the production of S. pneumoniae CPS 1 polysaccharide in E. coli. Production of S. pneumoniae CPS1 polysaccharide in E. coli. Western-blot analysis of proteinase K treated whole cell extracts from different E. coli strains transformed with plasmid pGVX767, containing complete CPS1 biosynthetic genes, wzg-ugd. Lanes 1, protein marker; lane 2, E. coli GVX2174 (W3110 ΔwaaL ΔwecAwzzECA ΔrfbO16::rfbP. shigelloidesO17-clmR); lane 3, E. coli GVX2174 transformed with pGVX767 (pLAFR encoding a promoter, a RBS, and wzg-ugd of CPS type 1); lanes 4 & 5, E. coli GVX3329 (=GVX2174 wbgW::clmR=W3110 ΔwaaL ΔwecAwzzECA ΔrfbO16::(rfbP.shigelloides O17 ΔwbgW::clmR)), transformed with pGVX767. Samples were run on 12% Bis-Tris gel (invitrogen) with MES for 35 min at 200V and then blotted in the iBlot and developed by anti-CP1 antibody (1:250) as a primary antibody. clmR denotes a DNA segment conferring chloramphenicol (clm) resistance, i.e. a clm resistance cassette.

Figure 7:
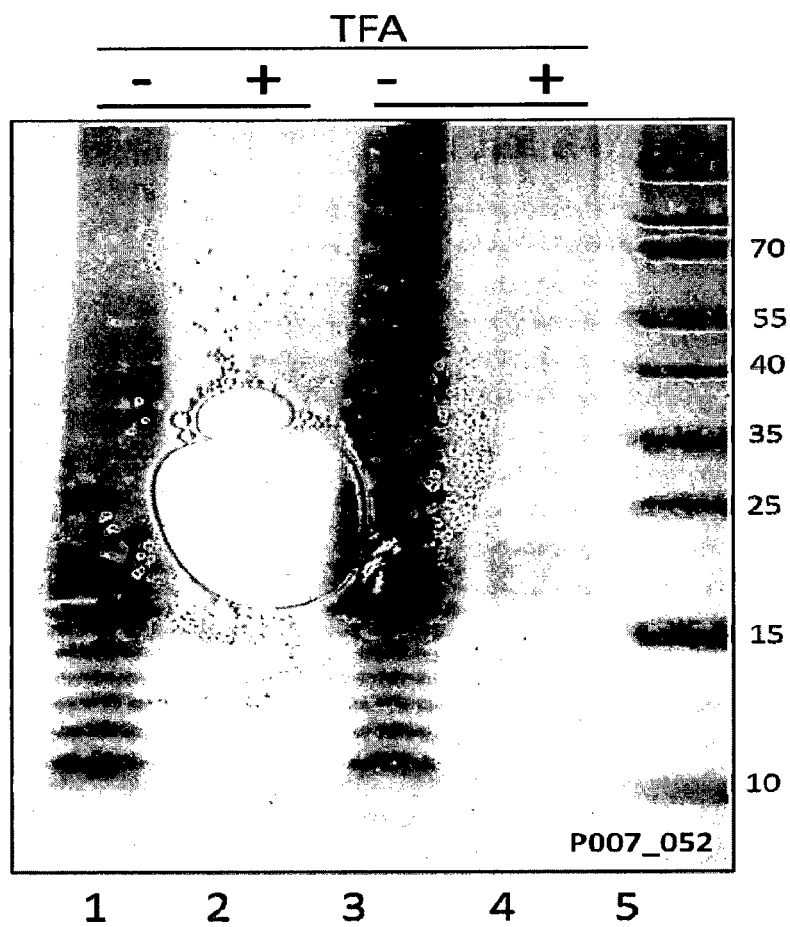

FIG. 7 Shows the sensitivity to acid treatment for CPS1 polysaccharide produced in E. coli. E. coli Western-blot analysis of E. coli GVX3329 transformed with plasmid pGVX767 (containing complete CPS1 biosynthetic genes, wzg-ugd). Lanes 1, 3, proteinase K treated of whole-cell extracts of two different colonies; lanes 2 & 4, TFA treated of corresponding extracts; lane 5, protein marker. Samples were run on a 12% Bis-Tris PAGE gels (invitrogen) with MES buffer for 35 min at 200V and then electroblotted and developed by anti-CP1 antibody (1:250) as a primary antibody.

Figure 8:
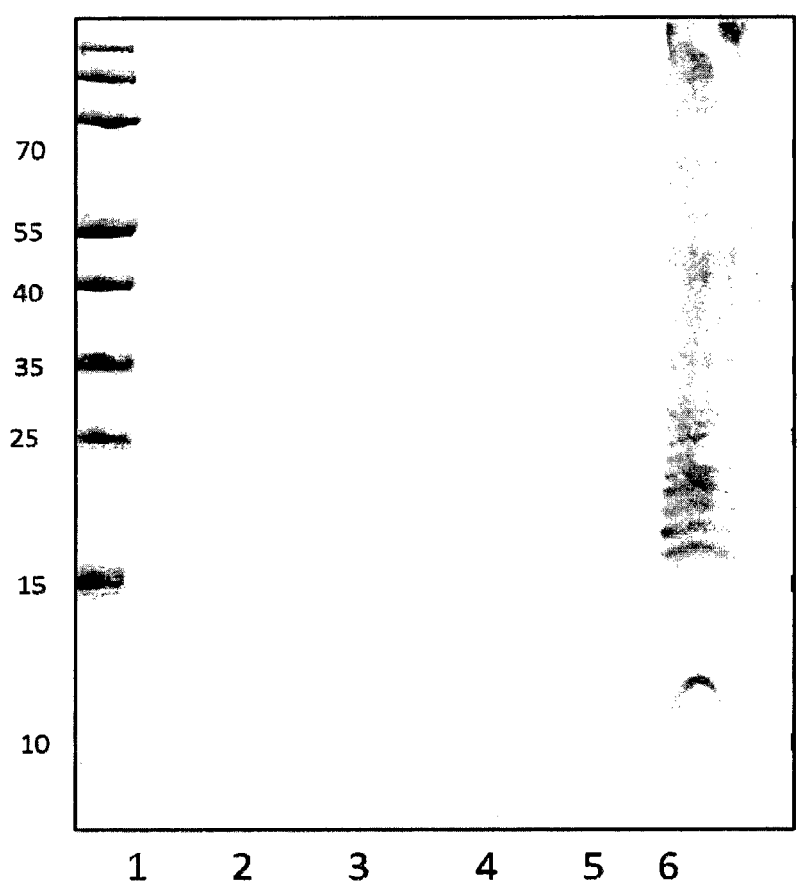

FIG. 8 Shows the effect of deletions of transporter genes in S. pneumoniae CPS1. Effect of deletion of capsular polysaccharide transporter genes, wzg, wzh, wzd, and wze, on biosynthesis of S. pneumoniae CPS1 polysaccharide in E. coli. Western-blot analysis of the whole cell extracts (proteinase K digested) of four different colonies of E. coli GVX3329 transformed with plasmid pGVX808 (=pGVX767 Δwzg-wze::clmR), lanes 2-5 and pGVX767 (complete CPS1 cluster), lane 6. Samples were run on 12% Bis-Tris gel (invitrogen) with MES for 35 min at 200V and then blotted in the iBlot and developed by anti-CP1 antibody (1:250) as a primary antibody.

Figure 9:
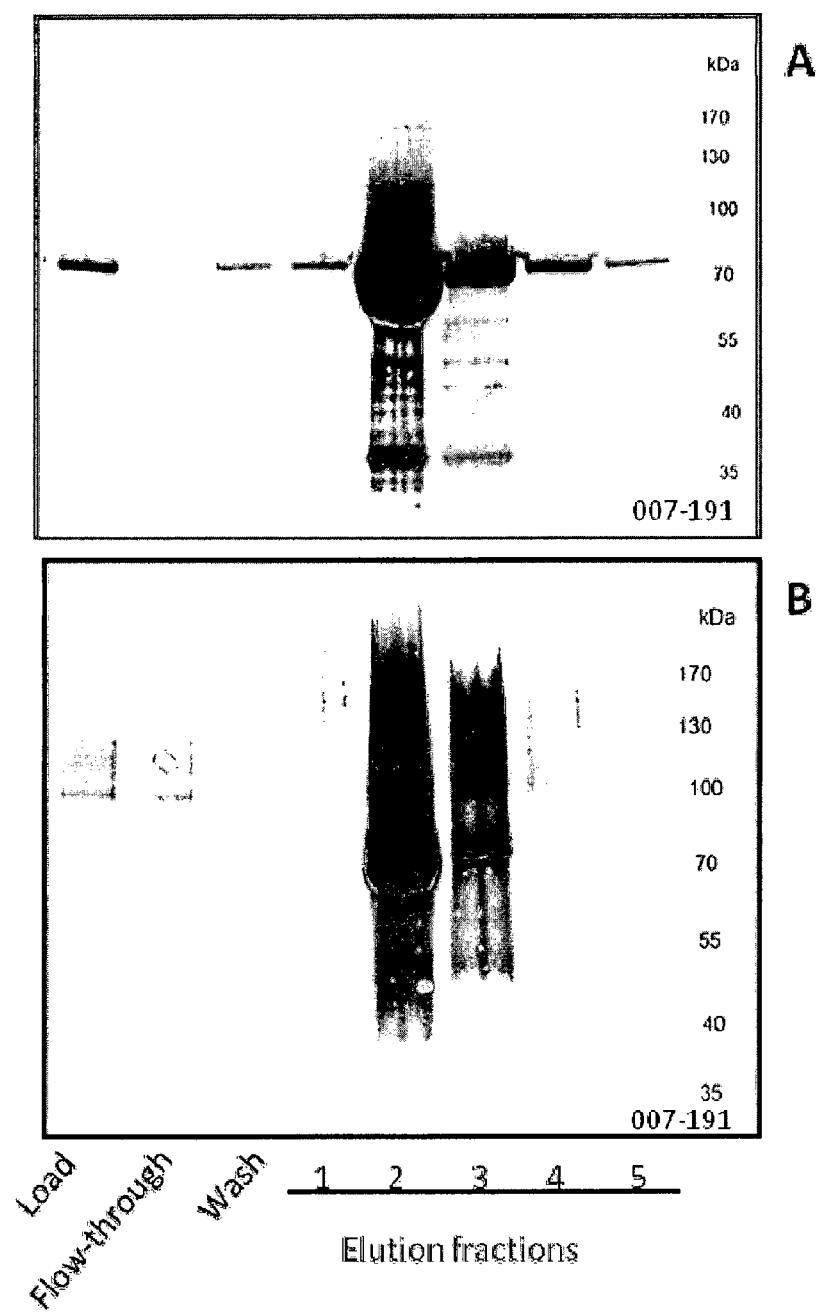

FIG. 9A and FIG. B His-Trap purification steps of N-glycosylated EPA with S. pneumoniae CPS type 1 from engineered E. coli. HisTrap purification steps of N-glycosylated EPA with S. pneumoniae capsular polysaccharide group 1 from engineered E. coli. FIG. 9A and FIG. 9B show western-blot of protein samples from purification steps of EPA-CP1 conjugates developed by anti-His and anti-CPL respectively. 4-12% Bis-Tris PAGE-gel used to resolve protein samples. E. coli strain GVX3329 (=GVX2174 wbgW::clmR=W3110 ΔwaaL ΔwecAwzzECA ΔrfbO16::(rfbP.shigelloidesO17 ΔwbgW::clmR)), transformed with pGVX767, pGVX114, and pGVX150 was used.

FIG. 10 Schematic diagram of a CPS4 subunit.

Figure 12:
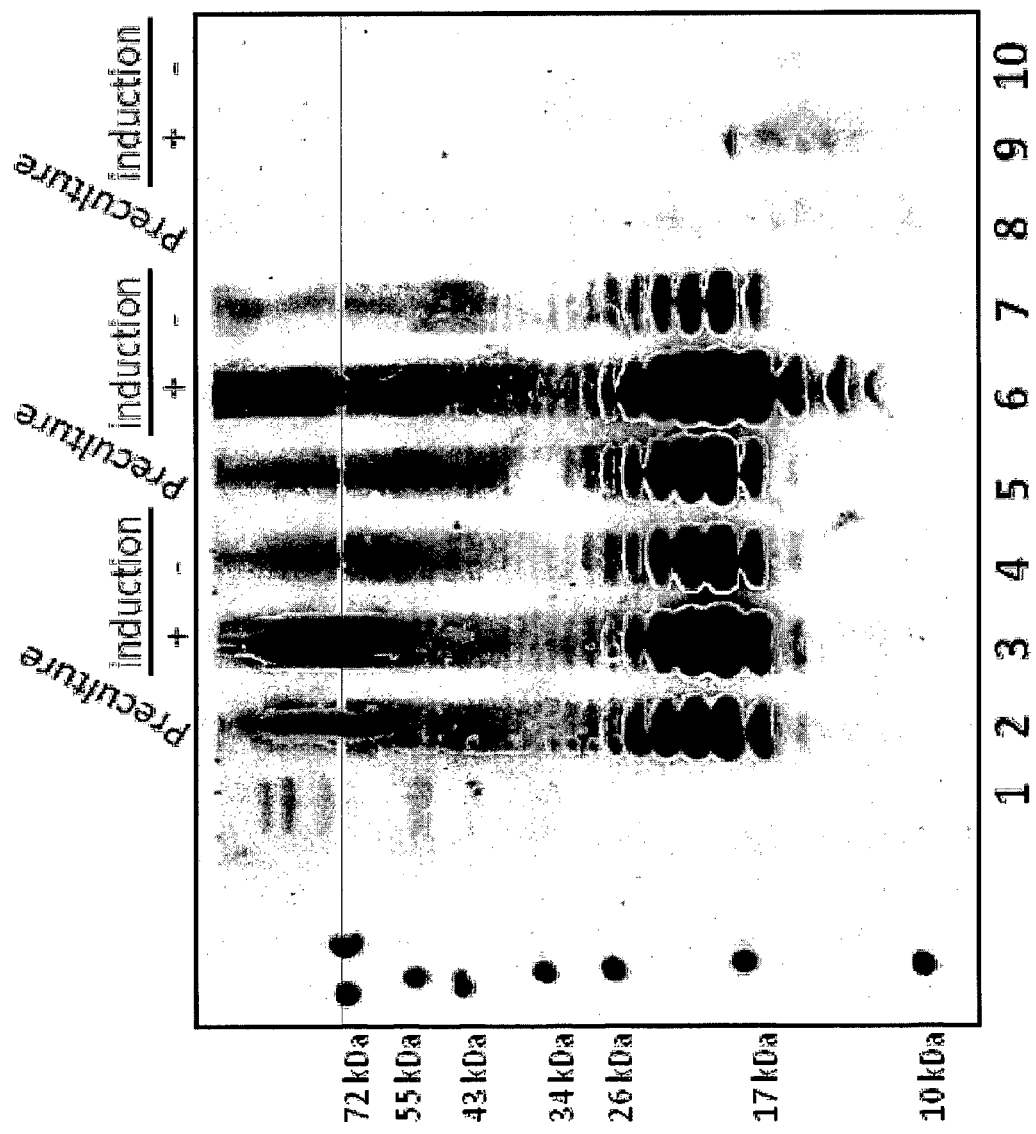

FIG. 11 CPS4 genetic organization. CPS4 genetic organization, wzg to fnlC are genes that are involved in biosynthesis of capsularpolysaccharide FIG. 12 Depicts the production of S. pneumoniae CPS4 polysaccharide in E. coli. Western-blot analysis of proteinase K treated whole cell extracts from different E. coli strains. Lane 1, protein marker; lanes 2-4, E. coli W3110 ΔwaaL transformed with pGVX803 (expressing the entire CPS4 cluster) and pGVX238 (Z3206, epimerase); lanes 5-7, E. coli W3110 ΔwaaL transformed with pGVX803 and pGVX207 (galE, epimerase); lanes 8-10, E. coli W3110 ΔwaaL E. coli transformed with pGVX753 (partial CPS4 cluster,wcij-fnlc, without regulatory genes and wciI) and pGVX238. 0.1% Arabinose as used for induction. Equivalents to 0.1 OD of cultured biomass were run on 12% Bis-Tris gel (invitrogen) with MES for 35 min at 200V and then blotted in the iBlot and developed by anti-CPS4 antibody (1:100) as a primary antibody.

Figure 13A:
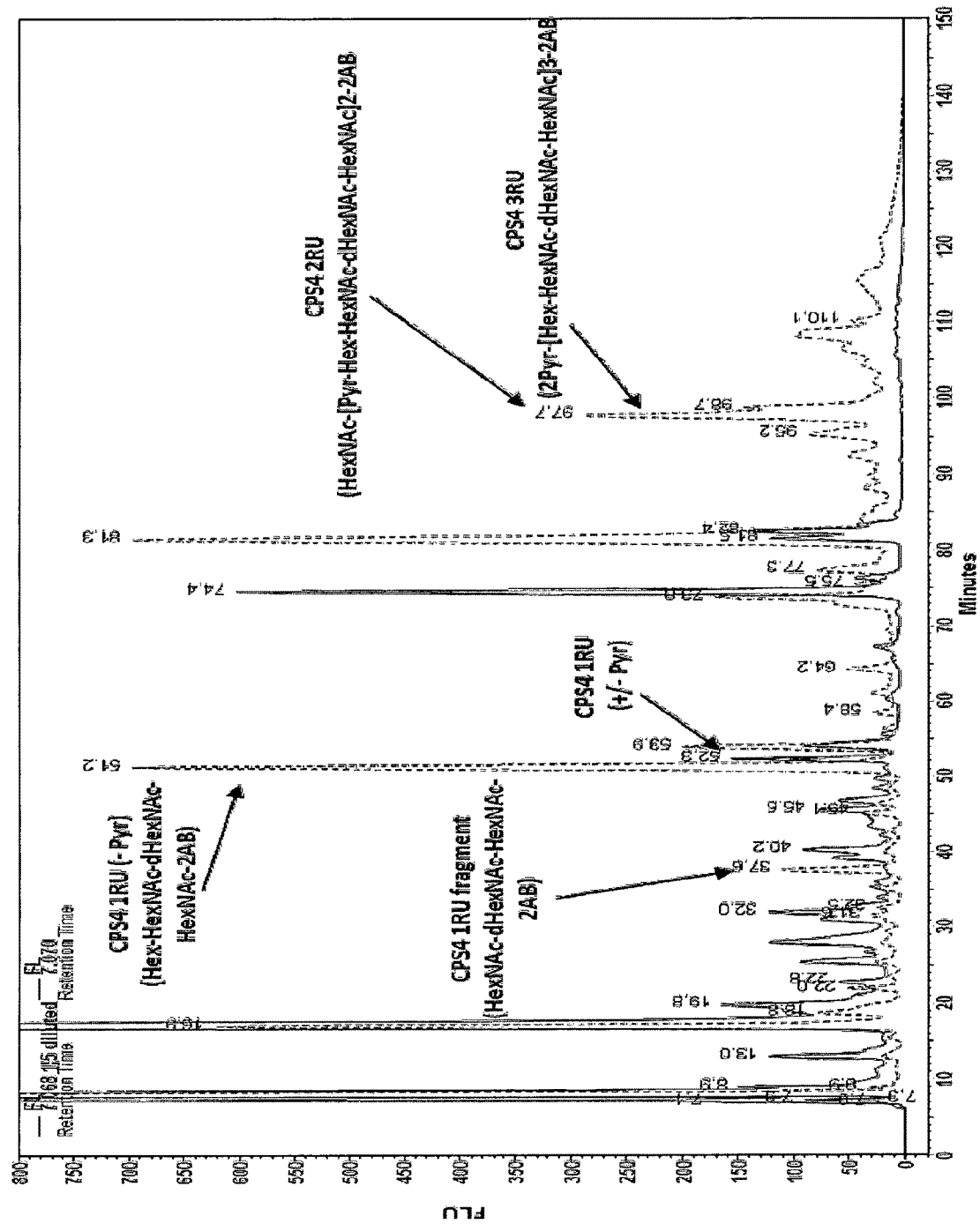
Figure 13B:
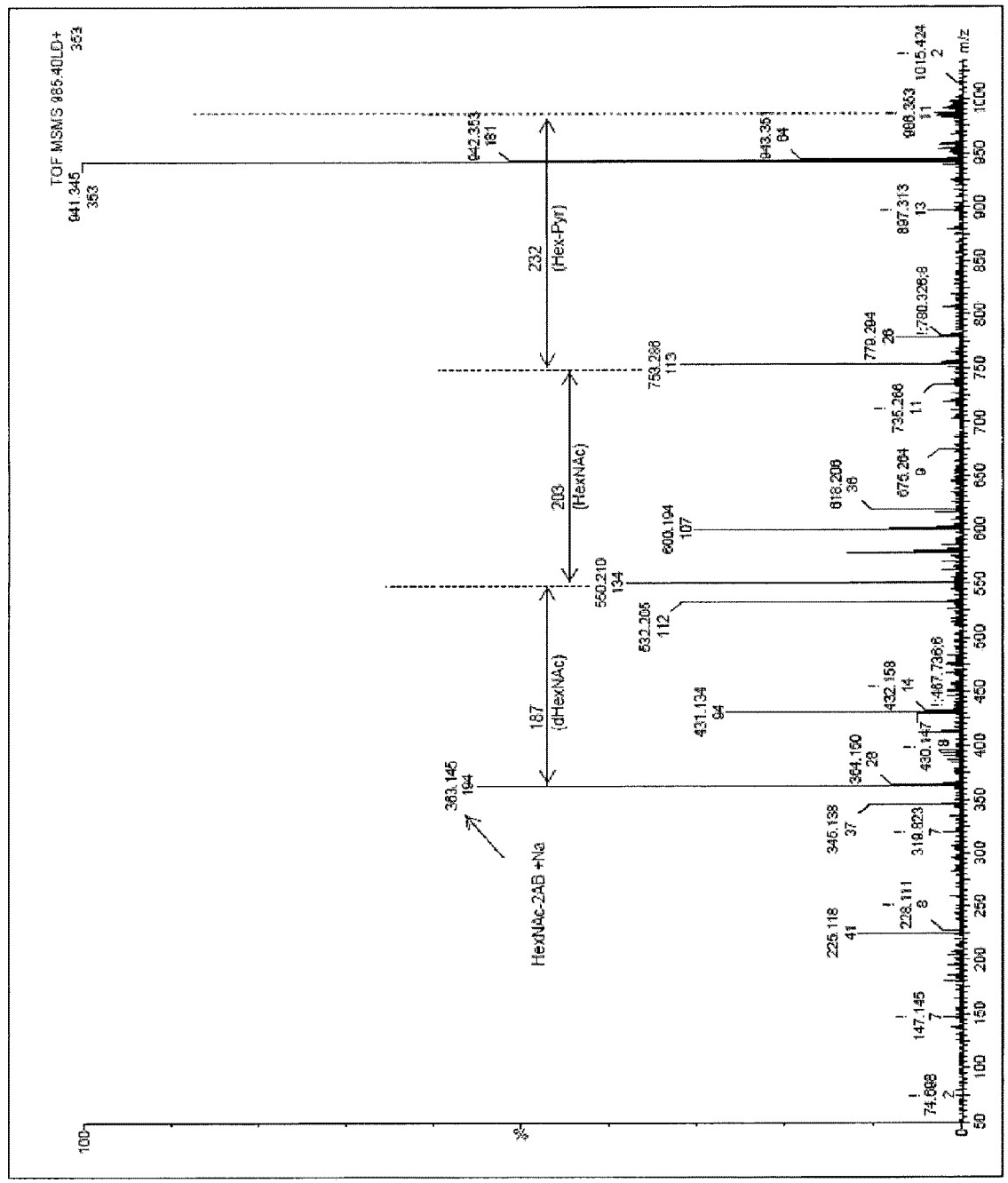

FIG. 13A and FIG. B Shows the results from the analysis of S. pneumoniae CPS4 produced in E. coli SCM6. Analysis of S. pneumoniae CPS4 produced in E. coli. LLO was extracted from E. coli SCM6 (Schwarz F, Huang W, Li C, Schulz B L, Lizak C, Palumbo A, Numao S, Neri D, Aebi M, Wang L X: A combined method for producing homogeneous glycoproteins with eukaryotic N-glycosylation. Nat Chem Biol 2010) and labeled with 2AB as described previously (US 2011/0274720 A1). FIG. 13A; chromatogram of 2AB labelled LLO extracted from E. coli SCM6 transformed with pGVX803 (expressing the entire CPS4 cluster from pLAFR) and galE epimerase (pGVX207, pMLBAD backbone), dashed lines, comparing to the background E. coli strain transformed with empty vectors pLAFR and pMLBAD, continuous line. FIG. 13B, MS/MS analysis of the single repeating unit of CPS4 peak which was eluted at 53.9 minutes, (FIG. 13A).

Figure 14:
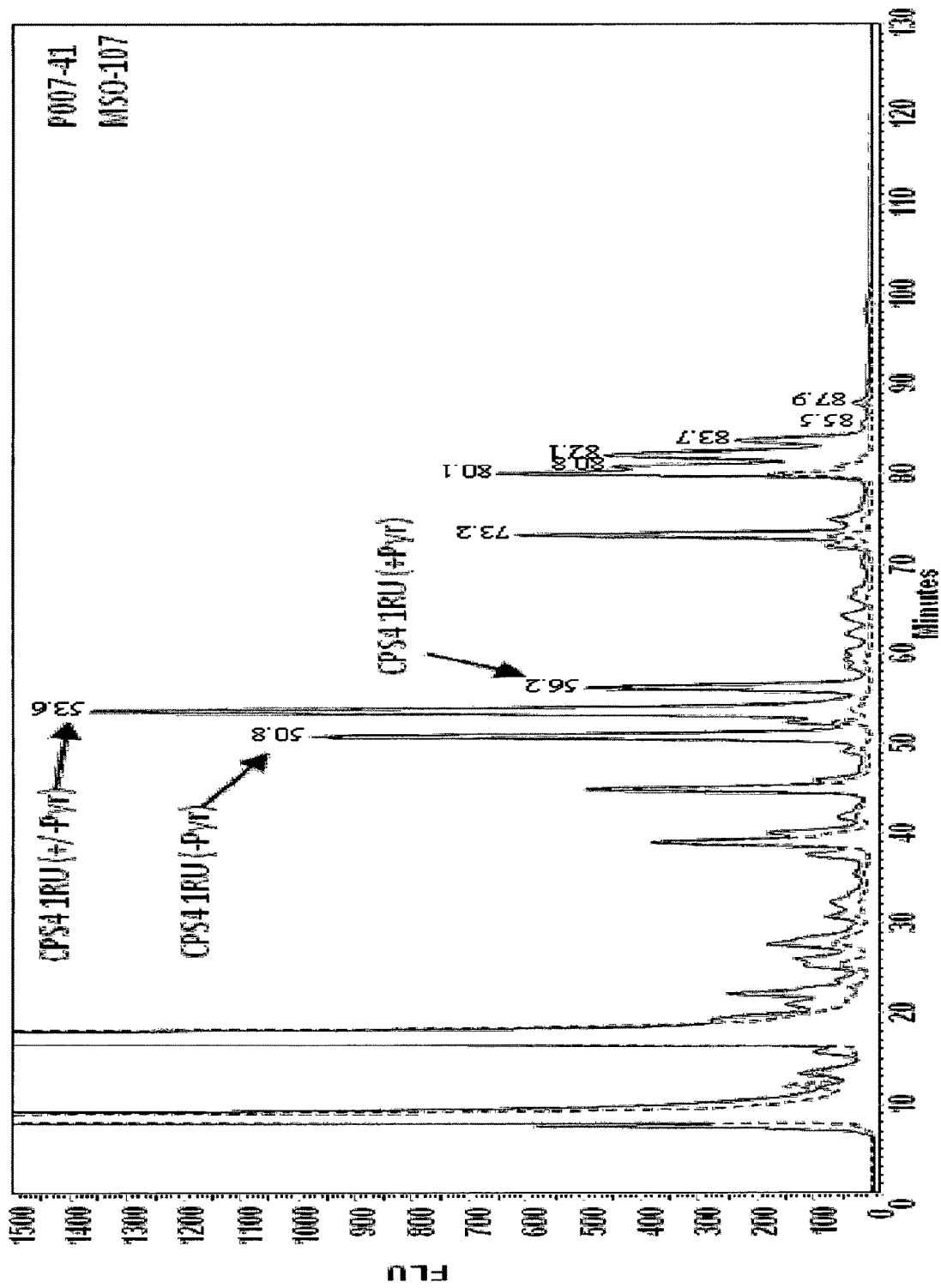

FIG. 14 Shows the results of the analysis of S. pneumoniae CPS4 produced in E. coli SCM3 (Faridmoayer A, Fentabil M A, Mills D C, Klassen J S, Feldman M F: Functional characterization of bacterial oligosaccharyltransferases involved in O-linked protein glycosylation. JOURNAL OF BACTERIOLOGY 2007, 189(22):8088-8098). Analysis of S. pneumoniae CPS4 produced in E. coli. LLO was extracted from E. coli SCM3 (Sφ874, ΔwaaL) and labelled with 2AB as described (US 2011/0274720 A1). HPLC chromatogram of 2AB labelled LLO extracted from E. coli SCM3 transformed with pGVX771 (pLAFR containing a promoter, RBS, the Z3206 gene, and wciJ-fnlc of the CPS14 cluster, without regulatory genes), solid line, comparing to the background E. coli SCM3 strain transformed with empty vector pGVX725 (pLAFR with promotor and RBS only), dashed line. MS analysis of peaks eluted at 50.8, 53.6 and 56.2 minute matched with a single CPS4 repeating unit (RU) with or without pyruvate (Pyr).

Figure 15A:
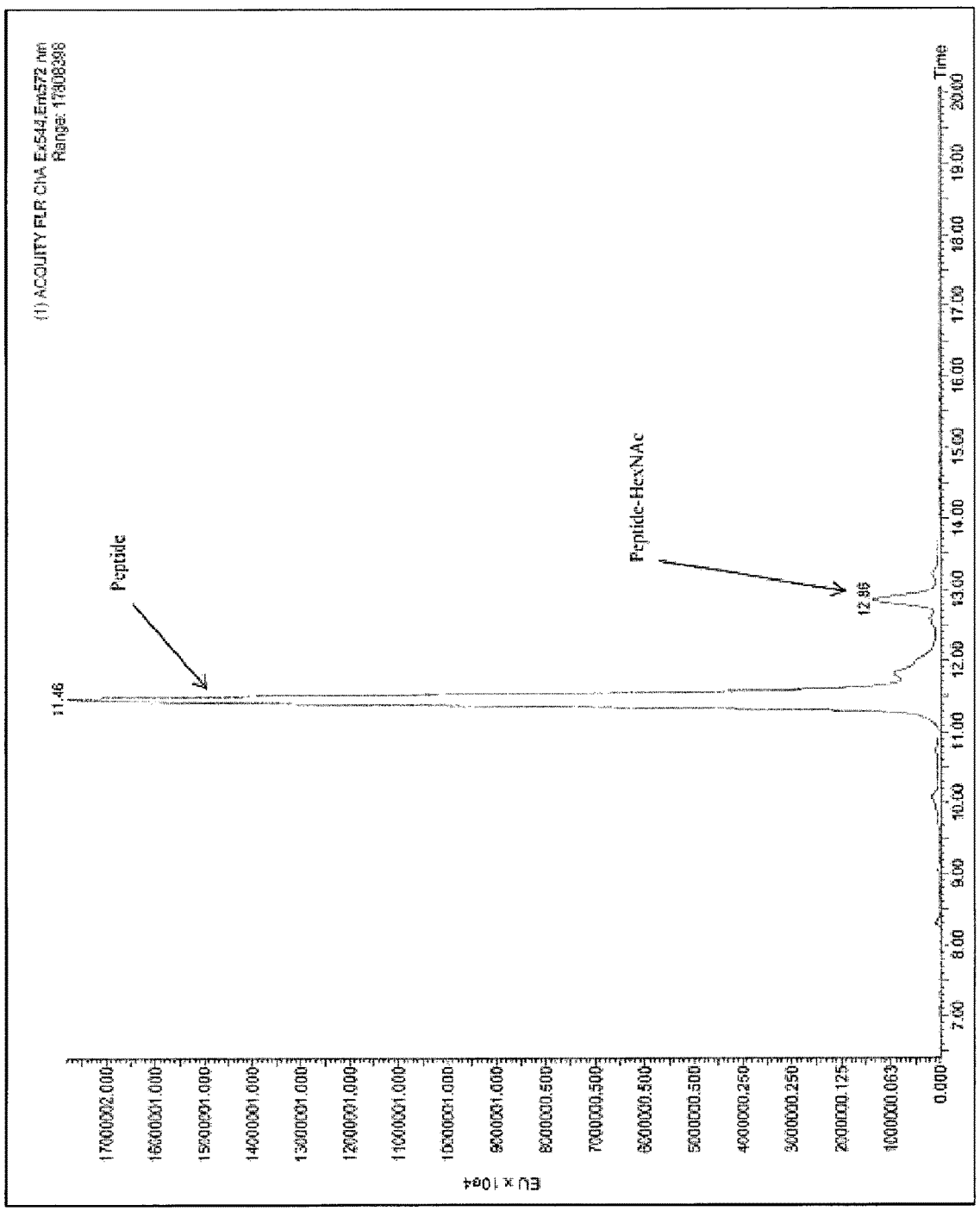
Figure 15B:
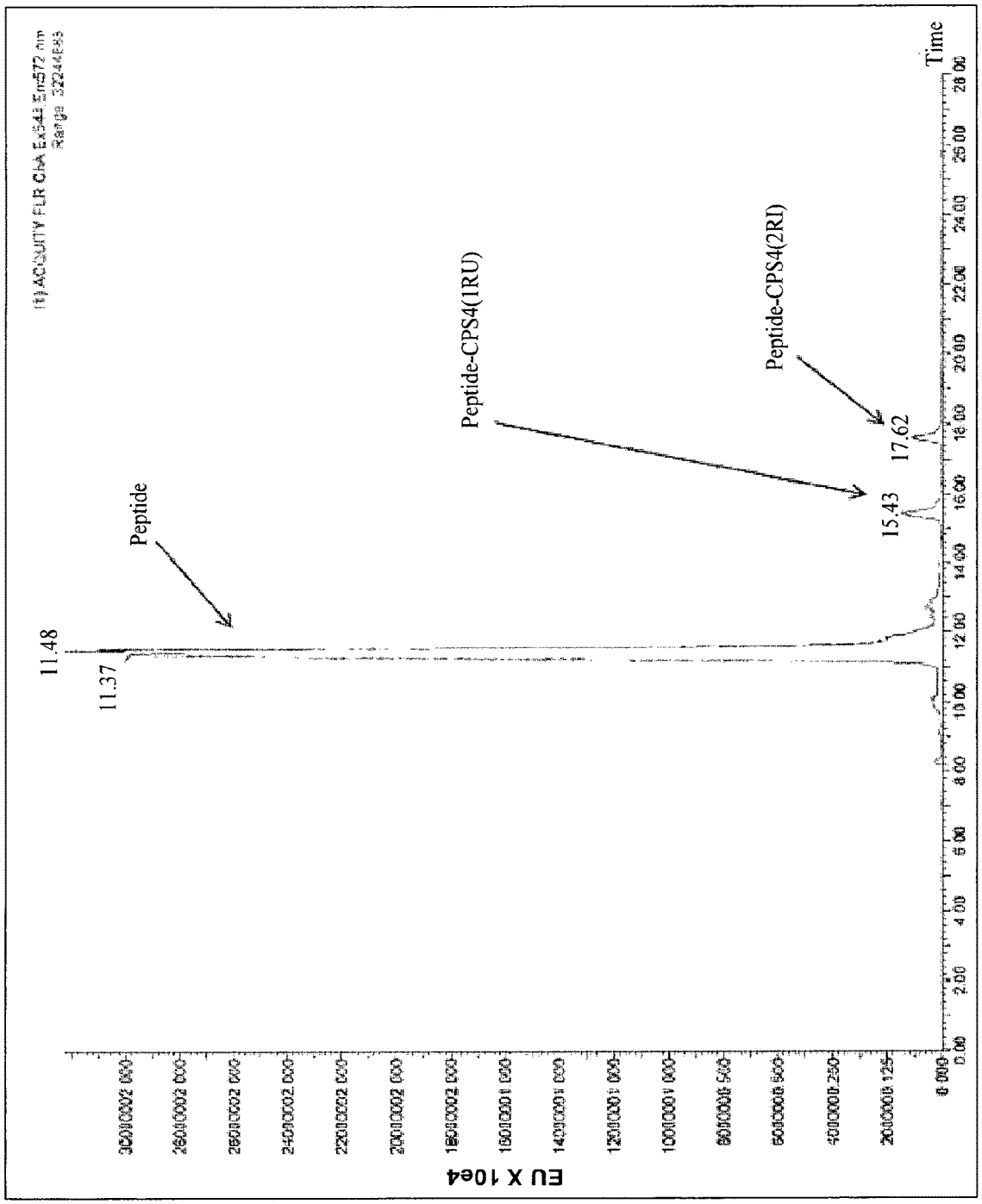
Figure 15C:
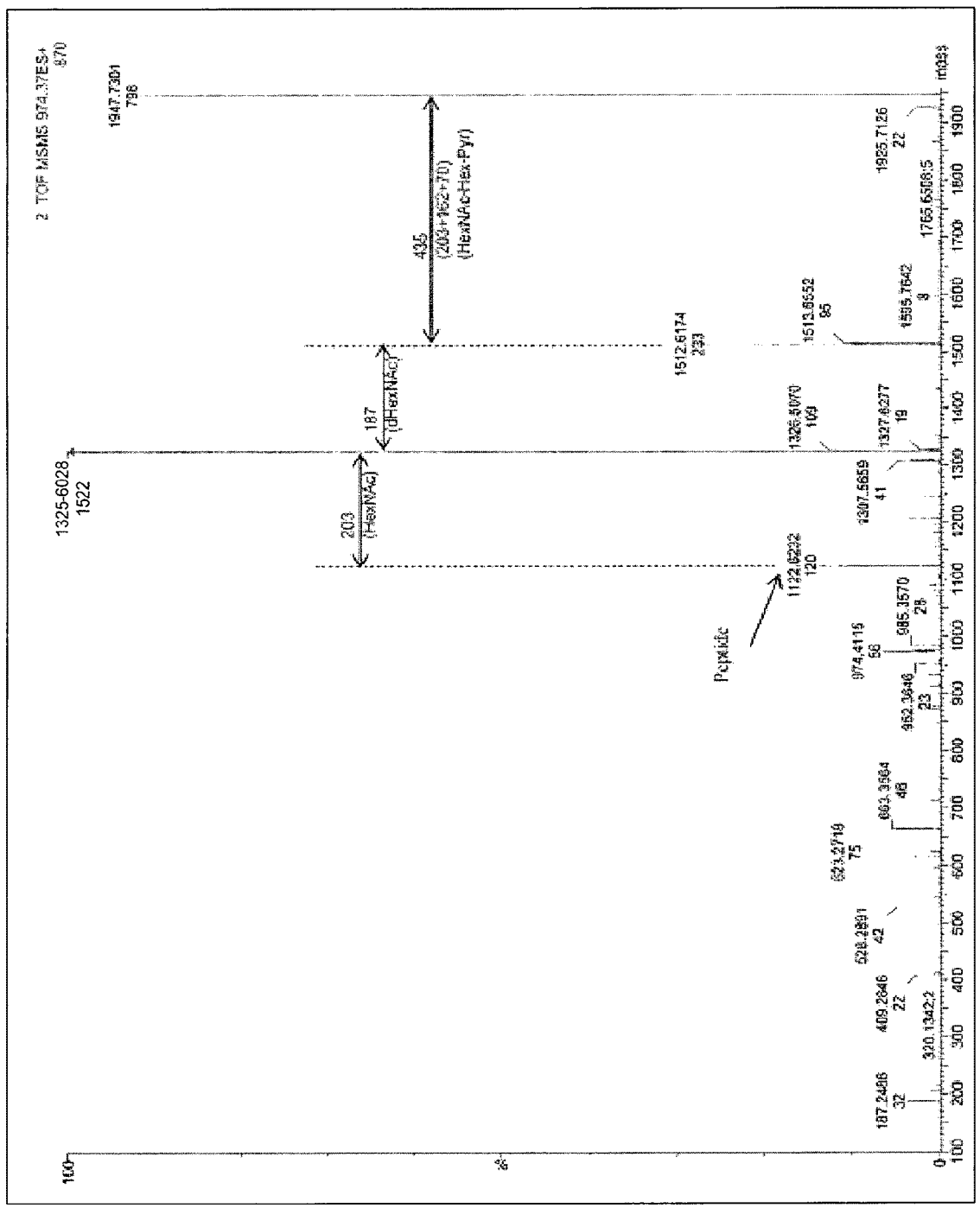
Figure 15D:
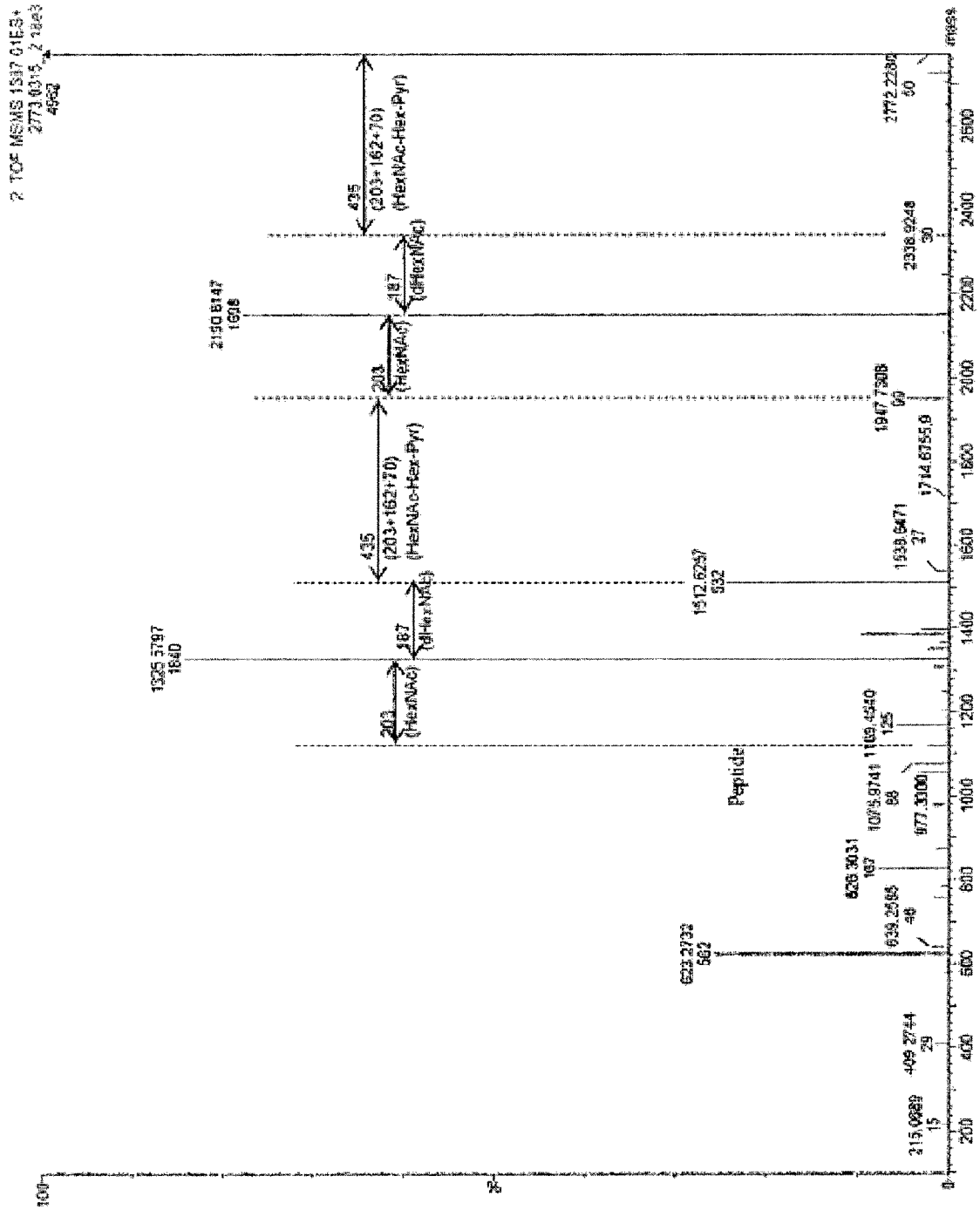

FIG. 15A-FIG. 15D Depicts the result from the analysis of the in vitro N-glycosylation using CPS4-LLO In vitro N-glycosylation using CPS4 lipid-linked oligosaccharide. LLO was extracted from *E. coli* SCM3 (Sφ874 ΔwaaL) transformed with pGVX771 (described in previous figure) and pGVX725 (empty vector). In vitro reaction was completed overnight by mixing purified *C. jejuni* PglB, a fluorescent-labeled peptide acceptor (Tamra-DANYTK) and LLO extract in a reaction buffer. Peptide was separated from reaction mixture by organic phase separation and subjected to UPLC followed by MS analysis. FIG. 15A and FIG. 15B, UPLC chromatograms of the peptide after glycosylation using LLO extracted from SCM3 containing pGVX725, (negative control), and SCM3 containing pGVX771. FIG. 15C and FIG. 15D, MS/MS analysis of the glycopeptides eluted at 15.43 and 17.62 minutes corresponding to one and two complete subunits of CPS4 assembled on the peptide.

FIG. 16A-C HisTrap purification steps of N-glycosylated EPA with *S. pneumoniae* CPS4 HisTrap purification steps of N-glycosylated EPA with *S. pneumoniae* CPS4 from engineered *E. coli*. *E. colicoli* W3110ΔwaaL transformed with pGVX539, pGVX114, pGVX207 and pGVX803 and grown in TB medium. FIGS. 16A, 16B, and 16C show coomassie stained and western-blot of protein samples from purification steps of EPA-CPS4 conjugates developed by anti-His and anti-CP4, respectively. 4-12% Bis-Tris SDS-gel used to resolve protein samples. pGVX539 is an expression plasmid for EPA carrier protein expression in which the EPA is detoxified and contains two N glycosylation consensus sequences.

Figure 17:
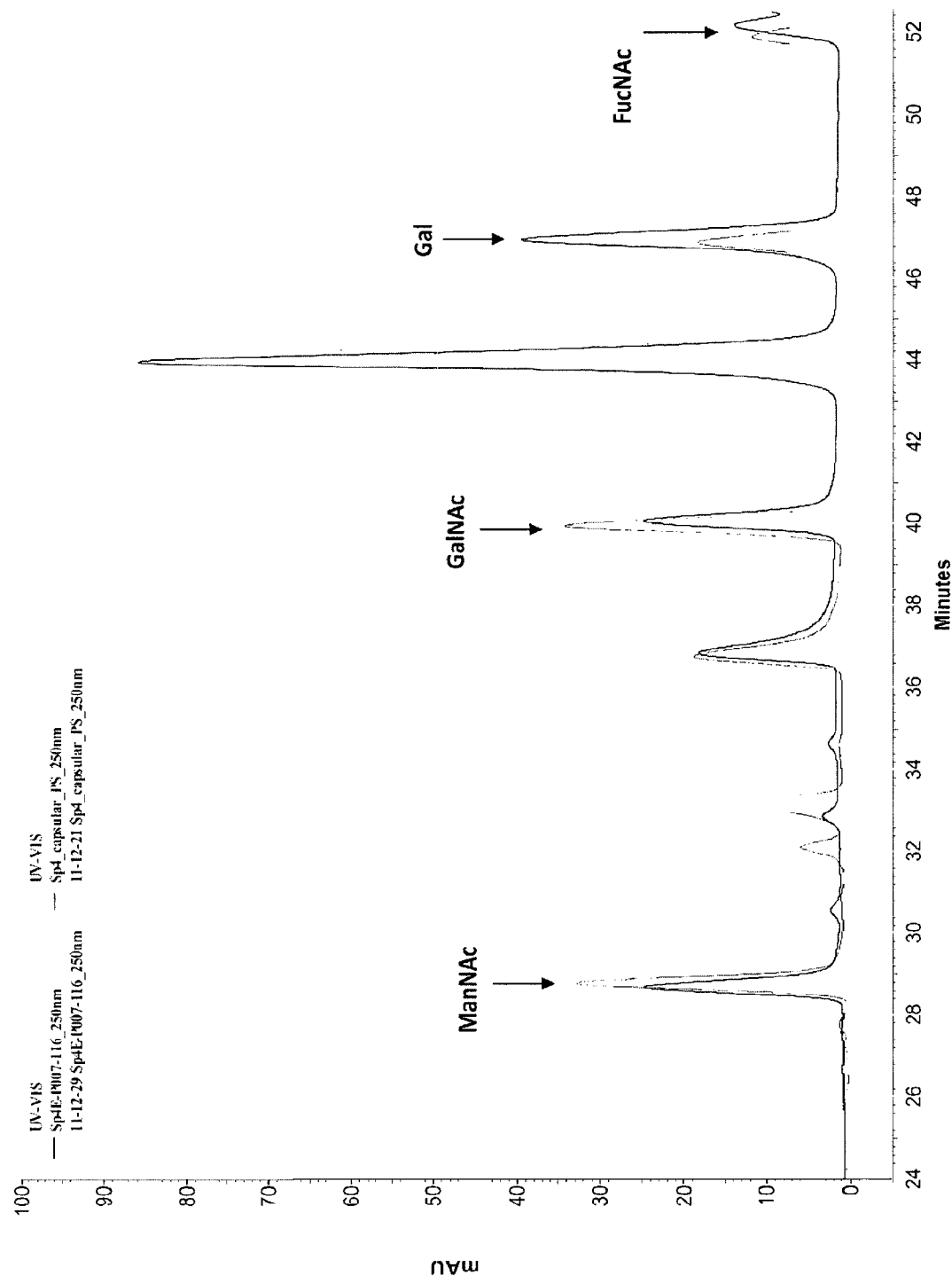
Figure 18:
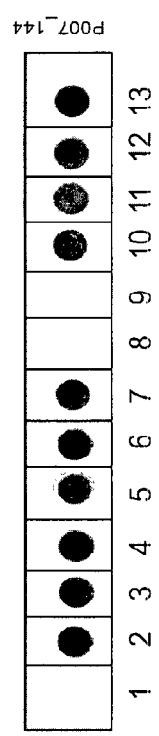

FIG. 17 Shows PMP derivatization analysis by HPLC RP analysis of CPS4-EPA glycoconjugates. PMP derivatization analysis by HPLC RP analysis of CPS4-EPA glycoconjugates produced in *E. coli*. Solid line: trace obtained from hydrolysis and analysis of glycoconjugate, dashed line: trace prepared identically from CP4 capsular polysaccharide FIG. 18 Depicts the Dot-blot analysis of sera from rabbits immunized with CPS4-EPA conjugates. Dot-blot analysis of sera from rabbits immunized with CPS4-EPA conjugates. 50 ng of CPS4 capsular polysaccharide isolated from *S. pneumoniae* group 4 was blotted on each spot. Sera obtained after second injection was used for the analysis with 1 to 100 dilution. Lane 1, pool of preimmune sera of rabbits that were used in this study; lanes 2-7, sera from different rabbits injected with EPA-CPS4; lanes 8-9, sera of control rabbits injected with buffer containing Aluminium hydroxide and Freund's complete adjuvans, respectively; Lane 10-11, sera of positive control rabbits injected with Prevenar-13; Lane 12-13, Pneumococoal antisera type 4 as a primary antibody from Statens serum institute with 1:100 and 1:200 dilutions, respectively were used.

Figure 19:
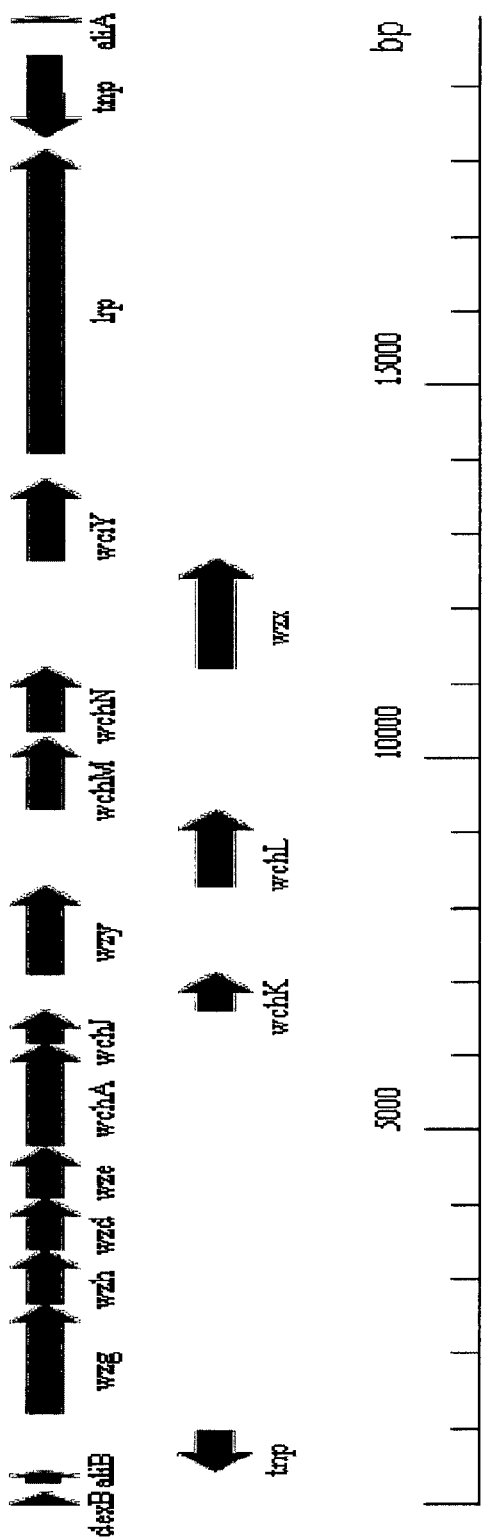

FIG. 19 Describes the CPS14 genetic organization of genes involved in the biosynthesis of CPS CPS14 genetic organization, wzg to wciY are genes that are involved in biosynthesis of capsularpolysaccharide.

Figure 20:
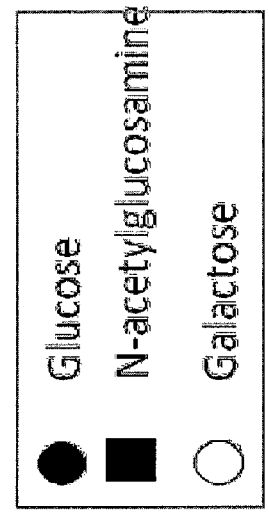

FIG. 20 Schematic diagram of a CPS14 subunit.

Figure 21A:
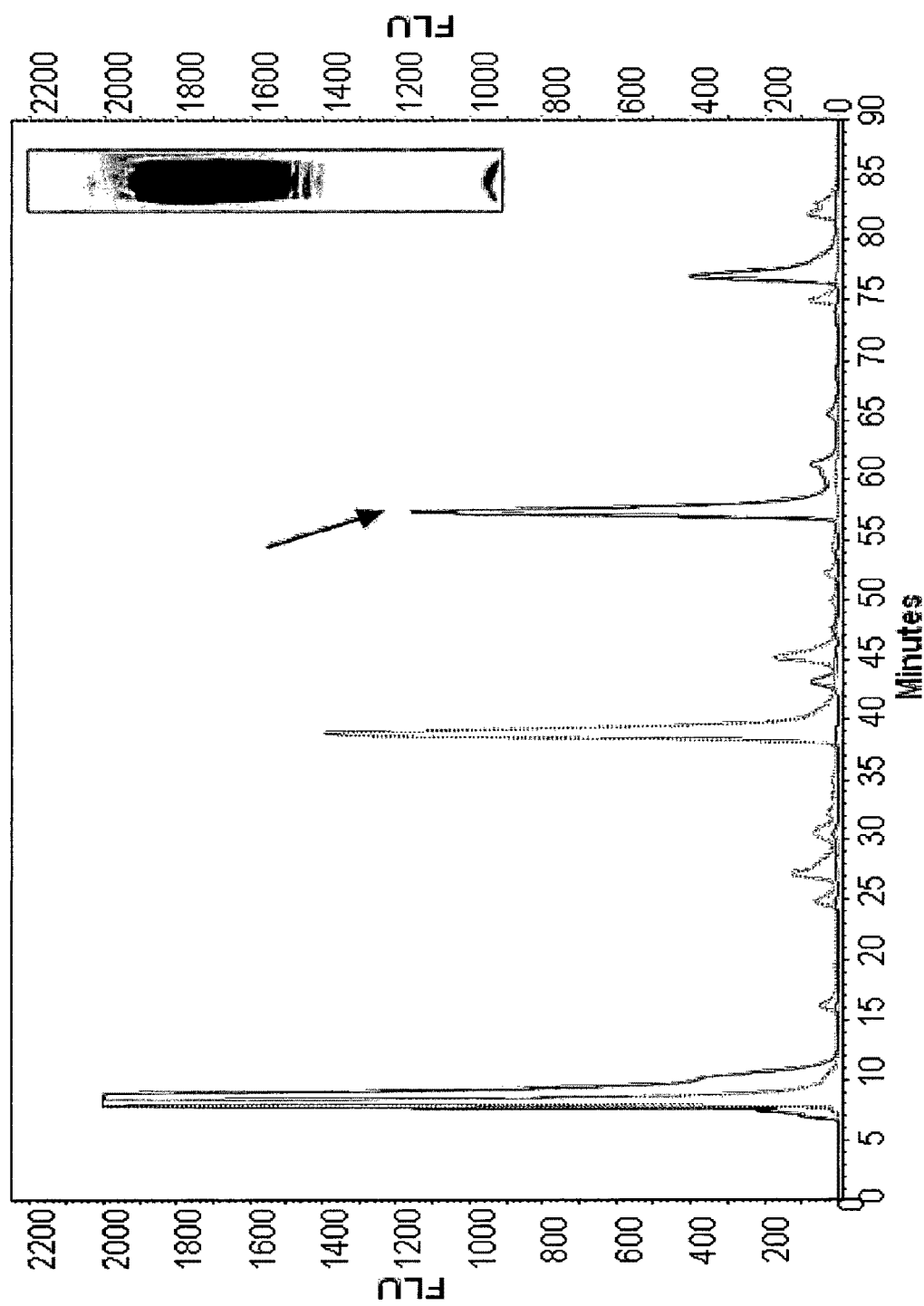
Figure 21B:
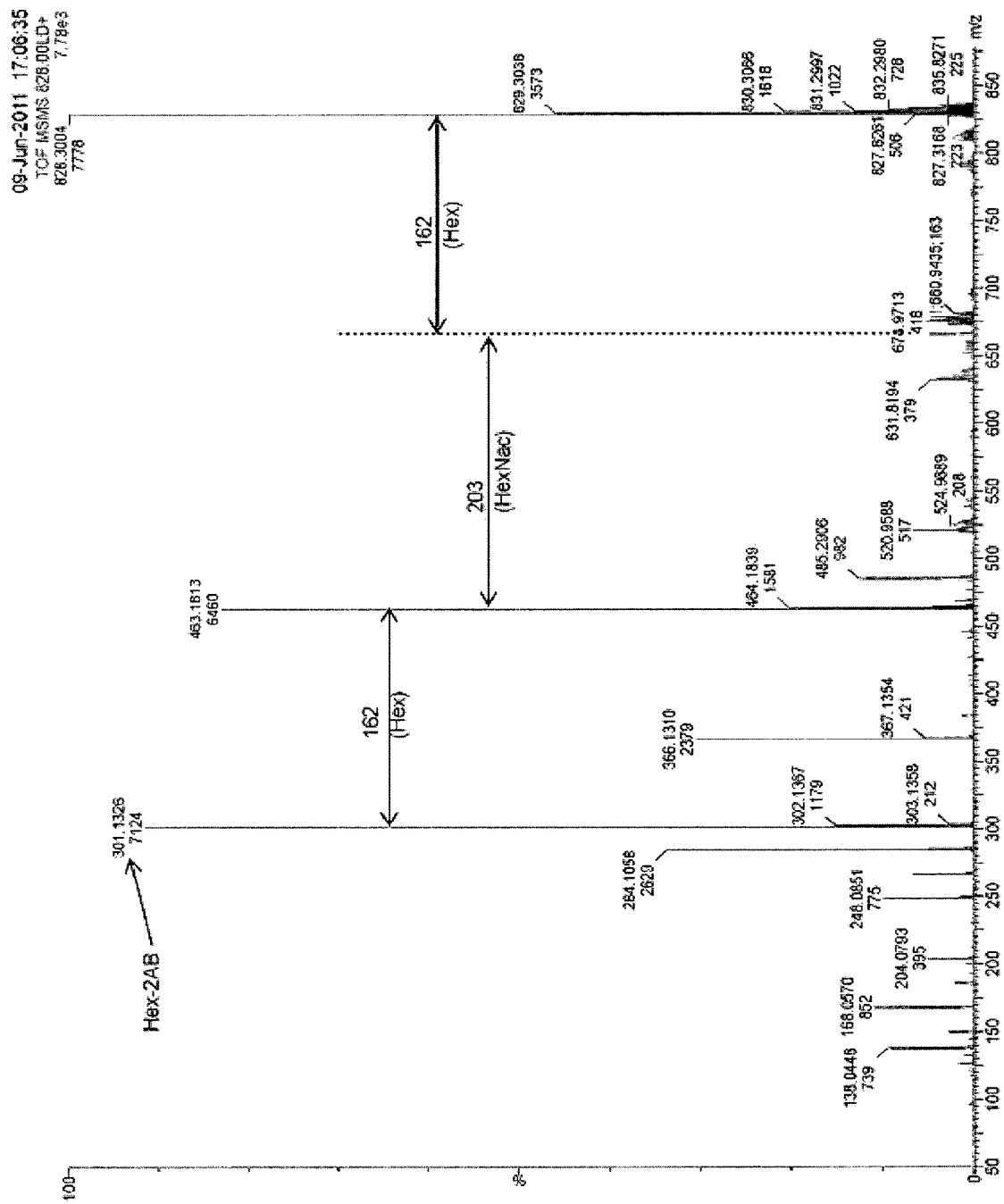

FIG. 21A and FIG. 21B Expression of CPS14 LLO in *E. coli*. wchA to wciY genes from CPS14 cluster were cloned into the gene replacement vector pDOC-C (pGVX615) containing O16 O antigen cluster (rfbO16) promoter and transformed into *E. coli* GVX1128 (W3110ΔwaaL). FIG. 21A, chromtogram of 2AB labeled LLO extracted from *E. coli* GVX1128 transformed with pGVX615wzy$_{mut}$ (CPS14 polymerase mutant producing a single subunit), solid line, comparing to LLO extracted from background strain, dashed line; inset is the western-blot of proteinase K digested *E. coli* GVX1128 transformed with pGVX615 probed by anti-CPS14 antibody as the primary antibody. FIG. 21B, MS/MS analysis of single subunit of CPS14 eluted at 57 minutes (indicated by arrow in FIG. 21A).

Figure 22:
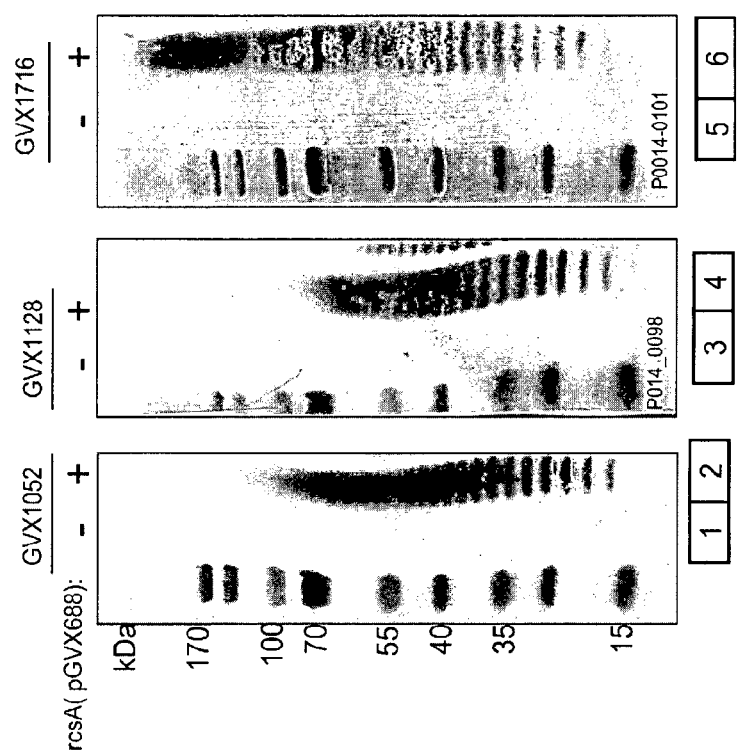

FIG. 22. Expression of CPS14 polysaccharide in *E. coli* strains in which colanic acid (CA) was replaced with the CPS14 cluster. Western-blot of proteinase K digested cells from different integrated *E. coli* strains probed by anti-CPS14 is depicted. All of the integrated strains; GVX6126 (GVX1052 CA::CPS14; lanes 1 & 2), GVX6129 (GVX1128 CA::CPS14; lanes 3 & 4), and GVX6300 (GVX1716; lanes 5 & 6), showed a ladder like pattern corresponding to production of CPS14 polymere when transformed with pGVX688, expressing RcsA.

Figure 23:
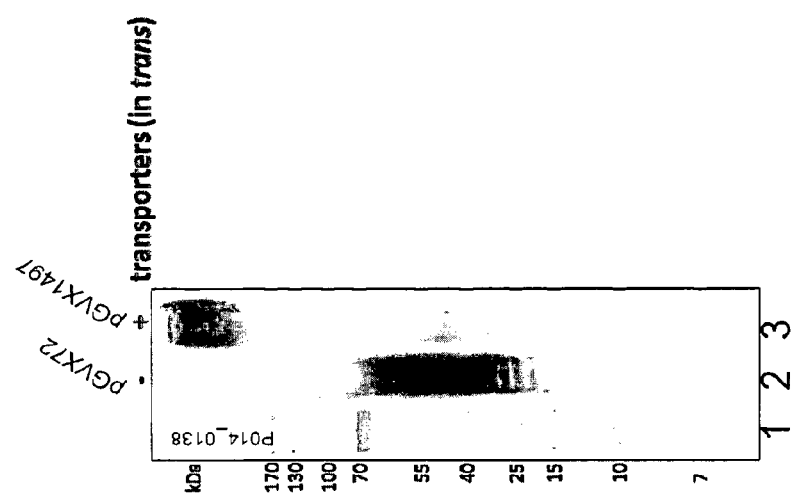

FIG. 23 Depicts the effect of CPS14 transporter genes on production of *S. pneumoniae* CPS14 polysaccharide in *E. coli* strains GVX6126 (*E. coli* W3110 CA::CPS14). Western-blot analysis of proteinase K treated whole cell extracts from different *E. coli* cells is shown. Lane 1, protein marker; lanes 2, *E. coli* GVX6126 transformed with pGVX688 (rcsA) and pGVX72 (empty vector; lanes 3, *E. coli* GVX6126 transformed with pGVX688 (rcsA) and pGVX1497 (CPS14 wzg-wze cloned into pGVX72). Equivalents to 0.4 OD of cultured biomass were run on 12% Bis-Tris gel (Invitrogen) with MES for 35 min at 200V and then blotted in the iBlot and developed by anti-CPS4 antibody (1:100) as a primary antibody.

FIG. 24 Depicts a chromtogram of 2AB labeled LLO extracted from *E. coli* GVX6129 (W3110ΔwaaL CA::CPS14) transformed with pGVXN688 (expressing RcsA) and glycolipids analyzed by 2-AB labeling and MS/MS analysis as described in sections 0079 and 0080. MS/MS analysis identified 2 and 3 subunits of CPS14, eluted at 95.9 min and 115.3, respectively (indicated by arrows).

5—DETAILED DESCRIPTION OF THE INVENTION

Pneumococcal capsular polysaccharides are synthetized on carrier lipids by the collaboration of a set of enzymes typically encoded in the CPS cluster of *S. pneumoniae* cells (Whitfield C, Roberts I S: Structure, assembly and regulation of expression of capsules in *Escherichia coli*. Mol Microbiol 1999, 31(5):1307-1319). The synthesis of wzy dependent CPS starts with the addition of a monosaccharide-phosphate to undecaprenylphosphate (Und-P) at the cytoplasmic side of the membrane. A short oligosaccharide is elongated by sequential addition of monosaccharides from activated sugar nucleotides by different glycosyltransferases and the lipid-linked polysaccharide is flipped through the membrane by a flippase. The antigen-repeating unit (RU) is polymerized by an enzymatic reaction performed by the protein wzy. The polysaccharide is then transferred to the final acceptor structure. Polymerization and transport to the cell surface is believed to be controlled by a set of 3 to 4 enzymes which are located at the 5' end of the CPS clusters.

Glycosyltransferases, polymerase wzy, flippase wzx, and the monosaccharide-phosphate transferases are encoded in most cases within the dexB to aliA cluster, whereas nucleotide activated monosaccharide biosynthetic pathways are encoded either elsewhere in the genome in the case of general housekeeping activities, and specifically within the CPS cluster when the monosaccharides are specific for the CPS (Bentley S D, Aanensen D M, Mavroidi A, Saunders D, Rabbinowitsch E, Collins M, Donohoe K, Harris D, Murphy L, Quail M A et al: Genetic analysis of the capsular biosynthetic locus from all 90 pneumococcal serotypes. *PLoS genetics* 2006, 2(3):e31).

Length control in CPS biosynthesis is believed to involve a circle of phosphorylation events for regulation (Morona J K, Miller D C, Morona R, Paton J C. The effect that mutations in the conserved capsular polysaccharide biosynthesis genes have on virulence of *Streptococcus pneumoniae. J Infect Dis.* 2004 May 15; 189(10):1905-13.Epub 2004 Apr. 27. PubMed PMID: 15122528). Most biosynthetic pathways producing CPS use nucleotide diphosphate (NDP) activated monosaccharides as substrates, namely this is UDP-Glc and UDP-GlcNAc. These NDP sugars are provided in Gram-negative and Gram-positive hosts by housekeeping genes, and thus are available as starting materials for synthesis of specific sugars. Biosynthetic genes for synthesis of specific NDP-sugars or other modifications are almost always encoded in CPS clusters.

O antigen synthesis and CPS synthesis differ at the last step of biosynthesis. O antigen is added to the Lipid A core by the ligase WaaL and is further transported to the outer membrane, whereas CPS is present as a capsular structure on the cells. In average, the final O antigen sugar length is much shorter than CPS.

*S. pneumoniae* CPS is classified as group I CPS due to the specific biochemical pathways leading to its synthesis. Gram-negative bacteria also contains group I CPS pathways, which differ from pneumococcal group I clusters by the presence of additional membrane transporter protein genes responsible for outer membrane transport. For example, these are the colanic acid (CA) biosynthetic machinery gene clusters wca, (Stevenson G, Andrianopoulos K, Hobbs M, Reeves P R: Organization of the *Escherichia coli* K-12 gene cluster responsible for production of the extracellular polysaccharide colanic acid. J Bacteriol 1996, 178(16):4885-4893) and the K30 CPS cluster (Whitfield C: Biosynthesis and assembly of capsular polysaccharides in *Escherichia coli. Annu Rev Biochem* 2006, 75:39-68).

However, despite the fact that some Gram-negative and positive capsular polysaccharide clusters were similar in functional elements, there was never an entire pneumococcal CPS cluster functionally expressed in *E. coli*. It is generally accepted that the different cell envelope architecture requires specific machinery for polysaccharide production, which is different when an outer membrane must be crossed. Thus described herein are improved production methods of pneumococcal capsular polysaccharides using i) aspects of the LPS and capsular polysaccharide pathways in a Gram-negative organism and ii) aspects of the Gram-positive capsular biosynthesis regulation and transport pathways in combination within Gram-negative host cells. Such polysaccharides are produced by LPS pathway mechanisms in the Gram-negative host, the structure of such polysaccharides are the same as LPS polysaccharides. Such polysaccharides produced in Gram-negative systems of the instant invention can be characterized, therefore, as "modified capsular polysaccharides" or "LPS capsules" for purposes of this application. Furthermore, this newly synthesized expression system and biosynthetic pathway, which combines the LPS and capsular biosynthetic pathways, may be characterized as being a "modified LPS biosynthetic pathway" for purposes of this application.

Accordingly, an additional embodiment involves an *S. pneumoniae* vaccine made by a glycosylation system using a modified LPS pathway, which comprises the production of a modified capsular polysaccharide or LPS-capsule.

Another specific embodiment of the invention involves the optimization of the gram negative *E. coli* host cell genome for optimized expression of the pneumococcal CPS. *E. coli* W3110 encodes a prophage gene cluster called gtr. The Gtr enzymes GtrA, B, and S encode a machinery that modifies O antigens by adding branching glucose residues to the growing O antigen chain in the periplasmic space (Lehane A M, Korres H, Verma N K: Bacteriophage-encoded glucosyltransferase GtrII of *Shigella flexneri*: membrane topology and identification of critical residues. The Biochemical journal 2005, 389(Pt 1):137-143). The pathway involves the generation of undecaprenylphosphate (Und-P, not Und-PP) linked glucose on the cytoplasmic face of the cell membrane, flipping to the periplasm, and consecutive transfer of the Und-P-linked glucose to the growing O antigen polysaccharide.

In certain embodiments, the gtrABS genes are partially or completely functionally inactivated or deleted from the Gram-negative host cell, e.g, gtrABS are deleted in an *E. coli* host cell. Without being bound by theory, such deletion channels all CPS biosynthetic activity to the glycosylation accessible Und-PP pathway and thereby enhances glycoprotein production. Many pneumococcal polysaccharides are synthesized as repeat unit (RU) polymers with glucose as the initiating monosaccharide. Thus, such repeat units may interfere with glycosylation of proteins as they are assembled on Und-P.

Another specific embodiment is the enhancement of Und-PP-linked CPS production by increasing the expression and activity of UDP-glucose:undecaprenyl phosphate glucose-phosphate transferase activity, which increases the Und-PP-Glc amounts in the cells and thus leads to enhanced production efficiency of CPS repeat unit (RU) and polysaccharides. Examples for such UDP-glucose:undecaprenyl phosphate glucose-phosphate transferases is the WchA of *S. pneumoniae* (i.e. the natural enzyme providing the initiator function) or the WcaJ encoded in the *E. coli* W3110 colanic acid wca operon. A specific embodiment of the invention is the replacement of the natural *S. pneumoniae* wchA gene function by the *E. coli* function encoded in the wcaJ gene for optimizing glycolipid production performance.

Another embodiment of the invention is the genomic integration of the recombinant CPS cluster in place of the *E. coli* W3110 wca operon for stable and high yield glycolipid production, and for enhanced glycosylation activity.

Regulatory Genes

Various regulatory genes of capsular polysaccharide gene clusters of Gram-positive bacteria can be used with the methods and host cells of the present invention. In specific embodiments, the regulatory gene is wzg, wzh, wzd, or wze of a capsular polysaccharide gene cluster of *S. pneumoniae*, or capA, capB, or capC of a capsular polysaccharide gene cluster of *S. aureus* or CpsA, CpsB, CpsC, or CpsD of a capsular polysaccharide gene cluster *Streptococcus agalactiae* (group B *Streptococcus*, or GBS). In certain embodiments, the regulatory gene is a regulatory gene of a capsular polysaccharide gene cluster listed in the Section "Capsular Polysaccharides" below.

Capsular Polysaccharides

In certain embodiments, the methods and host cells of the present invention are used to generate capsular polysaccharides of *S. pneumoniae*. These capsular polysaccharides include *S. pneumoniae* CPS1, CPS2, CPS3, CP4, CPS5, CPS6 (A and B), CPS7 (A,B, C), CPS8, CPS9 (A, L,N, V), CPS10 (A,B,C,F), CPS11 (A, B,C,D,F), CPS12(A,B,F), CPS13, CPS14 CPS15(A,B,C,F), CPS16(A,F), CPS17(A, F), CPS18(A,B,C,F), CPS19(A,B,C,F), CPS20, CPS21, CPS22(A,F), CPS23(A,B,F), CPS24(A,B,F), CPS25(A,F), CPS26, CPS27, CPS28(A,F), CPS29, CPS31, CPS32(A,F), CPS33(A,B,C,D,F), CPS34, CPS35(A,B,C,D,F), CPS36, CPS37, CPS38, CPS39, CPS40, CPS41(A,F), CPS42, CPS43, CPS44, CPS45, CPS46, CPS47(A,F), CPS48 and all the additional capsules as mentioned in (Bentley S D, Aanensen D M, Mavroidi A, Saunders D, Rabbinowitsch E, Collins M, Donohoe K, Harris D, Murphy L, Quail M A et al: Genetic analysis of the capsular biosynthetic locus from all 90 pneumococcal serotypes. *PLoS genetics* 2006, 2(3): e31). Specifically, these capsular polysaccharides include *S. pneumoniae* CPS1, CPS4, and CPS14.

In other embodiments, capsular polysaccharides of other Gram-positive bacteria can be generated using the methods and host cells of the present invention. Other Gram-positive bacteria include *Staphylococcus aureus* and *Streptococcus agalactiae* (GBS). Examples of such capsular polysaccharides include *S. aureus* CPS5, CPS8, *S. agalactiae* (group B, GBS) CPSIa, CPSIb, CPSII, CPSIII, CPSIV, CPSV, CPSVI, CPSVII, CPSVIII, *Enterococcus faecalis* CPSA, CPSB, CPSC, CPSD.

In certain embodiments, glycosyltransferases are introduced into the host cells provided herein such that a desired capsular polysaccharide is synthesized in the host cell. See, e.g., International Patent Application Application No. WO 2011/138361, which is hereby incorporated by reference in its entirety.

Bioconjugates

In certain embodiments of the present invention, the host cell is further modified to generate a bioconjugate, i.e., a carrier protein that is glycosylated with the capsular protein generated in the host cell. Transfer of the capsular polysaccharide onto the carrier protein is catalyzed by an oligosaccharyltransferase. In certain embodiments, an oligosaccharyltransferase is recombinantly expressed in the host cell. In certain embodiments, an oligosaccharyltransferase is introduced into the prokaryotic host. The oligosaccharyltransferases can be from any source, and may include heterologous oligosaccharyltransferases, i.e., oligosaccharyltransferases derived from a different organism than the prokaryotic host cell (e.g., oligosaccharyltransferases derived from a different bacterial species). In a specific embodiment, the oligosaccharyltransferase is from a *Campylobacter* species, e.g., *C. jejuni*.

The carrier protein can be a recombinant protein. In certain embodiments, the carrier protein is a protein that naturally comprises one or more N-glycosylation consensus sequences. In other embodiments, one or more N-glycosylation consensus sequences have been recombinantly introduced into the carrier protein. Any carrier protein suitable for use in the production of conjugate vaccines can be used herein. Exemplary carrier proteins include, without limitation, Exotoxin A of *P. aeruginosa* (EPA), CRM197, Diphtheria toxoid, tetanus toxoid, detoxified hemolysin A of *S. aureus*, clumping factor A of *S. aureus*, clumping factor B of *S. aureus*, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *C. jejuni* AcrA, and *C. jejuni* natural glycoproteins, *S. pneumoniae* pneumolysin and additional *S. pneumoniae* protein antigens, e.g., *S. pneumoniae* NOX, *S. pneumoniae* PspA, *S. pneumoniae* PcpA, *S. pneumoniae* PhtD, *S. pneumoniae* PhtE, *S. pneumoniae* Ply, and *S. pneumoniae* LytB.

In certain embodiments, the carrier proteins used in the generation of the conjugates described herein are modified, e.g., modified in such a way that the protein is less toxic and or more susceptible to glycosylation, etc. In a specific embodiment, the carrier proteins used in the generation of the conjugate vaccines described herein are modified such that the number of glycosylation sites in the carrier proteins is maximized in a manner that allows for lower concentrations of the protein to be administered, e.g., in an immunogenic composition, in its bioconjugate form. Accordingly in certain embodiments, the carrier proteins described herein are modified to include 1, 2, 3, 4, 5, 6, 7, 8, 9, 10, or more glycosylation sites than would normally be associated with the carrier protein (e.g., relative to the number of glycosylation sites associated with the carrier protein in its native/natural, e.g., "wild-type" state). In specific embodiments, introduction of glycosylation sites is accomplished by insertion of glycosylation consensus sequences anywhere in the primary structure of the protein. Introduction of such glycosylation sites can be accomplished by, e.g., adding new amino acids to the primary structure of the protein (i.e., the glycosylation sites are added, in full or in part), or by mutating existing amino acids in the protein in order to generate the glycosylation sites (i.e., amino acids are not added to the protein, but selected amino acids of the protein are mutated so as to form glycosylation sites). Those of skill in the art will recognize that the amino acid sequence of a protein can be readily modified using approaches known in the art, e.g., recombinant approaches that include modification of the nucleic acid sequence encoding the protein. In specific embodiments, glycosylation consensus sequences are introduced into specific regions of the carrier protein, e.g., surface structures of the protein, at the N or C termini of the protein, and/or in loops that are stabilized by disulfide bridges at the base of the protein. In certain embodiments, the classical 5 amino acid glycosylation consensus sequence may be extended by lysine residues for more efficient glycosylation, and thus the inserted consensus sequence may encode 5, 6, or 7 amino acids that should be inserted or that replace acceptor protein amino acids.

In certain embodiments, the carrier proteins used in the generation of the conjugate vaccines described herein comprise a "tag," i.e., a sequence of amino acids that allows for the isolation and/or identification of the carrier protein. For example, adding a tag to a carrier protein described herein can be useful in the purification of that protein and, hence, the purification of conjugate vaccines comprising the tagged carrier protein. Exemplary tags that can be used herein include, without limitation, histidine (HIS) tags (e.g., hexa histidine-tag, or 6×His-Tag), FLAG-TAG, and HA tags. In certain embodiments, the tags used herein are removable, e.g., removal by chemical agents or by enzymatic means, once they are no longer needed, e.g., after the protein has been purified.

In certain embodiments, the bacterial host cells described herein and the conjugates produced by such bacterial host cells described herein possess advantageous properties. For example, in certain embodiments, the bacterial host cells described herein, which comprise regulatory genes derived from Gram-positive bacteria, wherein said regulatory genes are involved in oligo- or polysaccharide biosynthesis, are able to produce sugar antigens, e.g., oligo- and/or polysaccharides, of increased length as a result of the presence of said regulatory genes. In addition, the bacterial host cells described herein are able to produce increased amounts of sugar antigens, e.g., oligo- and/or polysaccharides, as compared to Gram-negative bacterial host cells lacking regulatory genes derived from Gram-positive bacteria. Each of these characteristics is advantageous in that the conjugates produced by the bacterial cells have a higher sugar antigen to protein ratio and because the bacterial cells produce a greater number of conjugates.

In certain embodiments, a bacterial host cell described herein produces about 5%, 10%, 15%, 20%, about 25%, about 30%, about 40%, about 50%, or greater than 50% more conjugates than a bacterial host cell having the same properties but lacking a regulatory gene from a Gram positive bacteria that is involved in oligo- or polysaccharide biosynthesis. In certain embodiments, a bacterial host cell described herein produces 5% to 10%, 10% to 20%, 20% to 30%, 30% to 40%, or 40% to 50% more conjugates than a bacterial host cell having the same properties but lacking a regulatory gene from a Gram positive bacteria that is involved in oligo- or polysaccharide biosynthesis.

In certain embodiments, a bacterial host cell described herein produces about 5%, 10%, 15%, 20%, about 25%, about 30%, about 40%, about 50%, or greater than 50% more sugar antigens, e.g., oligo- and/or polysaccharides, than a bacterial host cell having the same properties but lacking a regulatory gene from a Gram positive bacteria that is involved in oligo- or polysaccharide biosynthesis. In certain embodiments, a bacterial host cell described herein produces 5% to 10%, 10% to 20%, 20% to 30%, 30% to 40%, or 40% to 50% more sugar antigens, e.g., oligo- and/or polysaccharides, than a bacterial host cell having the same properties but lacking a regulatory gene from a Gram positive bacteria that is involved in oligo- or polysaccharide biosynthesis.

In certain embodiments, a bacterial host cell described herein produces sugar antigens, e.g., oligo- and/or polysaccharides, that are about 5%, 10%, 15%, 20%, about 25%, about 30%, about 40%, about 50%, or greater than 50% longer than the sugar antigens, e.g., oligo- and/or polysaccharides produced by a bacterial host cell having the same properties but lacking a regulatory gene from a Gram positive bacteria that is involved in oligo- or polysaccharide biosynthesis. In certain embodiments, a bacterial host cell described herein produces sugar antigens, e.g., oligo- and/or polysaccharides, that are 5% to 10%, 10% to 20%, 20% to 30%, 30% to 40%, or 40% to 50% longer than the sugar antigens, e.g., oligo- and/or polysaccharides produced by a bacterial host cell having the same properties but lacking a regulatory gene from a Gram positive bacteria that is involved in oligo- or polysaccharide biosynthesis.

Various assays can be used to characterize the conjugates described herein, e.g., characterize the carrier protein, attached sugar antigen(s) (e.g., oligo- and/or polysaccharide), or both, including, e.g., high performance size exclusion chromatography, isoelectric focusing, SDS-PAGE and Western Blot, molecular weight determination by MS, N terminal sequencing, amino acid analysis, reverse phase liquid chromatography, electrospray mass spectroscopy, tandem mass spectrometry (MS/MS), and peptide mapping by mass spectroscopy after tryptic digestion.

EMBODIMENTS

In one embodiment, provided herein is an engineered Gram-negative bacterium for the production of a polysaccharide, wherein the Gram-negative bacterium comprises a regulatory gene of a capsular polysaccharide gene cluster of a Gram-positive bacterium. In certain embodiments, the Gram-negative bacterium comprises at least 25%, 50%, 75%, 85%, 90%, or at least 95% of the open reading frames of the capsular polysaccharide gene cluster. In certain embodiments, the Gram-negative bacterium comprises a complete capsular polysaccharide gene cluster. In certain embodiments, the polysaccharide comprises an epitope of the capsular polysaccharide.

In certain embodiments, the Gram-negative bacterium of the preceding paragraph is selected from the group consisting of *Escherichia* species, *E. coli*, *Shigella* species, *Klebsiella* species, *Salmonella* species, *Yersinia* species, *Neisseria* species, *Vibrio* species and *Pseudomonas* species. In a specific embodiment, the Gram-negative bacterium is *E. coli*.

In certain embodiments, the regulatory gene of a capsular polysaccharide gene cluster of a Gram-positive bacterium that is engineered into the Gram-negative bacterium of any one of the preceding paragraphs is a *Streptococcus pneumoniae* regulatory gene. In a specific embodiment, the *S. pneumoniae* regulatory gene is from *S. pneumoniae* Type 1. In a specific embodiment, the *S. pneumoniae* regulatory gene is from *S. pneumoniae* Type 4.

In certain embodiments, the regulatory gene of a capsular polysaccharide gene cluster of a Gram-positive bacterium that is engineered into the Gram-negative bacterium of any one of the preceding paragraphs is a *Staphylococcus aureus* regulatory gene. In a specific embodiment, the regulatory gene is a *Staphylococcus agalactiae* regulatory gene.

In certain embodiments, the regulatory gene of a capsular polysaccharide gene cluster of a Gram-positive bacterium that is engineered into the Gram-negative bacterium of any one of the preceding paragraphs is an *Enterococcus faecalis* regulatory gene.

In certain embodiments, the Gram-negative bacterium of any of the preceding paragraphs comprises an oligosaccharyl transferase. In a specific embodiment, the oligosaccharyl transferase is heterologous to the Gram-negative bacterium.

In certain embodiments, the Gram-negative bacterium of any of the preceding paragraphs comprises at least one heterologous glycosyltransferase. In a specific embodiment, the heterologous glycosyltransferase is a prokaryotic glycosyltransferase. In a specific embodiment, the glycosyltransferase is obtained from the same Gram-positive bacterium as the regulatory gene.

In certain embodiments, the Gram-negative bacterium of any of the preceding paragraphs comprises a deletion or inactivation of one or more genes native to the Gram-negative bacterium. In a specific embodiment, the one or more deleted genes comprise the waaL gene. In a specific embodiment, the one or more deleted genes comprise all genes associated with O antigen biosynthesis in the Gram-negative bacterium.

In certain embodiments, the regulatory gene engineered into the Gram-negative bacterium of any of the preceding paragraphs is wzg, wzh, wzd, wze, capA, capB, or capC.

In certain embodiments, the Gram-negative bacterium of any of the preceding paragraphs comprises a nucleic acid encoding a carrier protein comprising a consensus sequence for glycosylation. In a specific embodiment, the nucleic acid encoding the carrier protein is heterologous to the Gram-negative bacterium. In a specific embodiment, the carrier protein is detoxified exotoxin A from *P. auruginosa*, CRM197, Diphtheria toxoid, tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* sat protein, the passenger domain of *E. coli* sat protein, *C. jejuni* AcrA, *C. jejuni* natural glycoproteins, and *S. pneumoniae* pneumolysin. In a specific embodiment, the carrier protein is an *S.* pneumoniae protein, e.g., *S. pneumoniae* pneumolysin, *S. pneumoniae* NOX, *S. pneumoniae* PspA, *S. pneumoniae* PcpA, *S. pneumoniae* PhtD, *S. pneumoniae* PhtE, *S. pneumoniae* Ply, or *S. pneumoniae* LytB. In a specific embodiment, the carrier protein is conjugated to the polysaccharide by an oligosaccharyl transferase.

In certain embodiments, the regulatory gene engineered into the –negative bacterium of any of the preceding paragraphs is a regulatory gene corresponding to one of the following capsular polysaccharide gene clusters: *S. pneumoniae* CPS1, CPS2, CPS3, CP4, CPS5, CPS6 (A and B), CPS7 (A,B, C), CPS8, CPS9 (A, L,N, V), CPS10 (A,B,C,F), CPS11 (A, B,C,D,F), CPS12(A,B,F), CPS13, CPS14 CPS15 (A,B,C,F), CPS16(A,F), CPS17(A,F), CPS18(A,B,C,F), CPS19(A,B,C,F), CPS20,CPS21, CPS22(A,F), CPS23(A,B, F), CPS24(A,B,F), CPS25(A,F), CPS26, CPS27,CPS28(A, F), CPS29, CPS31, CPS32(A,F), CPS33(A,B,C,D,F), CPS34, CPS35(A,B,C,D,F), CPS36, CPS37, CPS38, CPS39, CPS40, CPS41(A,F), CPS42, CPS43, CPS44, CPS45, CPS46, CPS47(A,F), or CPS48; or *Staphylococcus aureus* CPS5, or CPS8; *Streptococcus agalactiae* (group B, GBS) CPSIa, CPSIb, CPSII, CPSIII, CPSIV, CPSV, CPSVI, CPSVII, or CPSVIII; or *Enterococcus faecalis* CPSA, CPSB, CPSC, or CPSD.

In one embodiment, provided herein is a vector capable of replication in a Gram-negative bacterium, wherein said vector comprises a regulatory gene associated with capsular polysaccharide biosynthesis in a Gram-positive bacterium.

In certain embodiments, the expression and activity of UDP-glucose:undecaprenyl phosphate glucose-phosphate transferase activity is increased in the Gram-negative bacterium of any of the preceding paragraphs.

In certain embodiments, Gram-negative bacterium of any of the preceding paragraphs expresses WcaJ encoded by colanic acid wca operon of an enterocommonbacteriae (e.g., *E. coli* W3110).

In certain embodiments, provided herein is an engineered Gram-negative bacterium for the production of a polysaccharide, including a Gram-negative bacterium of any of the preceding paragraphs, wherein a gene encoding a Gtr enzyme of the Gram-negative bacterium is functionally inactivated. In a specific embodiment, functional inactivation of the gene encoding a Gtr enzyme results in elimination of Und-P linked glucose. In a specific embodiment, the gene encoding a Gtr enzyme of the Gram-negative bacterium is deleted. In a specific embodiment, the genes encoding GtrA, GtrB, and/or GtrS are functionally inactivated. In a specific embodiment, the genes encoding GtrA, GtrB, and/or GtrS are deleted. In a specific embodiment, the Gram-negative bacterium is selected from the group consisting of *Escherichia* species, *E. coli*, *Shigella* species, *Klebsiella* species, *Salmonella* species, *Yersinia* species, and *Pseudomonas* species.

In a specific embodiment, the Gram-negative bacterium of the preceding paragraph comprises an oligosaccharyl transferase. In a specific embodiment, the oligosaccharyl transferase is heterologous to the Gram-negative bacterium.

In a specific embodiment, the Gram-negative bacterium of the preceding paragraphs comprises at least one glycosyltransferase that is heterologous to the Gram-negative bacterium. In a specific embodiment, the glycosyltransferase is a prokaryotic glycosyltransferase.

In a specific embodiment, the Gram-negative bacterium of the preceding paragraphs comprises a nucleic acid encoding a carrier protein comprising a consensus sequence for glycosylation. In a specific embodiment, the nucleic acid encoding the carrier protein is heterologous to the Gram-negative bacterium. In a specific embodiment, the carrier protein is detoxified exotoxin A from *P. auruginosa*, CRM197, Diphtheria toxoid, tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* sat protein, the passenger domain of *E. coli* sat protein, *C. jejuni* AcrA, and *C. jejuni* natural glycoproteins. In a specific embodiment, the carrier protein is conjugated to the polysaccharide by the oligosaccharyl transferase.

In a specific embodiment, the polysaccharide of the Gram-negative bacterium of the preceding paragraphs is a capsular polysaccharide of *Streptococcus pneumoniae*.

In a specific embodiment, the polysaccharide of the Gram-negative bacterium of the preceding paragraphs is an O antigen of *E. coli* (O1, O2, O3, O4, O5, O6, O7, O8, O9, O10, O11, O12, O13, O14, O15, O16, O17, O18, O19, O20, O21, O22, O23, O24, O25, O26, O27, O28, O29, O30, O32, O33, O34, O35, O36, O37, O38, O39, O40, O41, O42, O43, O44, O45, O46, O48, O49, O50, O51, O52, O53, O54, O55, O56, O57, O58, O59, O60, O61, O62, O63, O64, O65, O66, O68, O69, O70, O71, O73, O74, O75, O76, O77, O78, O79, O80, O81, O82, O83, O84, O85, O86, O87, O88, O89, O90, O91, O92, O93, O95, O96, O97, O98, O99, O100, O101, O102, O103, O104, O105, O106, O107, O108, O109, O110, O111, O112, O113, O114, O115, O116, O117, O118, O119, O120, O121, O123, O124, O125, O126, O127, O128, O129, O130, O131, O132, O133, O134, O135, O136, O137, O138, O139, O140, O141, O142, O143, O144, O145, O146, O147, O148, O149, O150, O151, O152, O153, O154, O155, O156, O157, O158, O159, O160, O161, O162, O163, O164, O165, O166, O167, O168, O169, O170, O171, O172, O173, O174, O175, O176, O177, O178, O179, O180, O181, O182, O183, O184, O185, O186, O187), *Salmonella* sp (*S. enterica* subsp. *Enterica*, *S. enterica* subsp. *Salamae*, *S. enterica* subsp. *arizonae*, *S. enterica* subsp. *Diarizonae*, *S. enterica* subsp. *Houtenae*, *S. bongori*, and *S. enterica* subsp. Indica, and O types 1-67, *Pseudomonas* sp (*P. aeruginosa* O serotypes 1-20), *Klebsiella* sp. (particularly *K. pneumonia* serotypes O1, O2 (and subserotypes), O3, O4, O5, O6, O7, O8, O9, O10, O11, O12), Acinetobacter O antigens (in particular *A. baumannii* O antigens), *Chlamydia trachomatis* O antigens (serotypes A, B, C, D, E, F, G, H, I J, K, L1, L2, L3), *Vibrio cholera* O antigens O1 to 155, *Listeria* sp., in particular *L. monocytogenes* type 1, 2, 3, 4 and subserotypes thereof, *Legionella pneumophila* serotypes 1 to 15 O antigens, *Bordetella parapertussis* O antigens, *Burkholderia mallei* and *pseudomallei* O antigens, *Francisella tularensis*, *Campylobacter* sp. (*C. jejuni*); Capsular polysaccharides of *Clostridium difficile* (serotypes A, G, H, K, S1, S4, D, Cd-5, and *C. perfringens* serotypes A, B, C, D and E), *Staphylococcus aureus* type 5 and 8, *Streptococcus pyrogens* (group B streptococcus capsular serotype polysaccharides), *E. coli*, *Streptococcus agalacticae* (group A streptococcal capsular polysaccharides), *Neisseria meningitidis* (serotypes A, B, C, W, Y, X), *Candida albicans*, *Haemophilus influenza*, *Enterococcus faecalis* capsular polysaccharides type I-V; and other surface polysaccharide structures, e.g. the *Borrelia burgdorferi* glycolipids), *Neisseria meningitidis* pilin O glycan and lipooligosaccharide (LOS), *Haemophilus influenza* LOS, Leishmania major lipophosphoglycan, tumor associated carbohydrate antigens, malaria glycosyl phosphatidylinositol, or *Mycobacterium tuberculosis* arabinomannan.

In specific embodiments, provided herein is a recombinant glycoprotein produced by the Gram-negative bacterium of any one of the preceding paragraphs.

In specific embodiments, provided herein is a method of producing a recombinant glycoprotein comprising culturing the Gram-negative bacterium of any one of the preceding paragraphs under conditions suitable for the production of proteins. In a specific embodiment, the method further comprises purifying the recombinant glycoprotein.

In a specific embodiment, provided herein is an engineered *E. coli* cell comprising a *Plesiomonas shigelloides* O antigen gene cluster wherein the wbgW gene of the O antigen gene cluster is inactivated and wherein the *E. coli* cell produces Und-PP-D-FucNAc4N.

In a specific embodiment, provided herein is an engineered *E. coli* cell comprising a *Shigella sonnei* or *Plesiomonas shigelloides* O17 O antigen gene cluster wherein the wbgW gene of the O antigen gene cluster is inactivated and wherein the *E. coli* cell produces Und-PP-D-FucNAc4N.

6—EXAMPLES

Example 1: Synthesis of CPS1 Conjugates in *E. coli*

A goal of an embodiment of the invention is to produce the CPS type 1 antigenic polysaccharides in *E. coli*. As discussed above, we exploited in a novel way, the ability of *E. coli* to express the biosynthetic machinery of the *S. pneumoniae* CPS cluster.

The CPS cluster DNA (as defined by the DNA sequence between dexB and aliA) is depicted in FIG. 2 and the repeat unit structures of *S. pneumoniae* Type 1 are shown in FIG. 3. The repeat unit starts with a D-FucNAc4N, followed by two D-GalA residues linked in alpha 1-3 glycosidic linkages (-4-a-D-GalA-1,3-a-D-GalA-1,3-a-D-FucNAc4N-). In addition, the RU is non-stoechiometrically O-acetylated (Bentley S D, Aanensen D M, Mavroidi A, Saunders D, Rabbinowitsch E, Collins M, Donohoe K, Harris D, Murphy L, Quail M A et al: Genetic analysis of the capsular biosynthetic locus from all 90 pneumococcal serotypes. PLoS genetics 2006, 2(3):e31). The DNA sequence contains putative genes encoding proteins for:

i) transport/regulation (Wzg, Wzh, Wzd, Wze), ii) two glycosyltransferases most probably responsible for transfer of the two GalA residues (WchBD), as concluded form homology searches iii) a putative acetyltransferase WchC, iv) a polymerase wzy, for polymerization of repeat units on the outer leaflet of the cytoplasmic membrane v) a flippase wzx, to flip single repeat units from the inner to the outer leaflet of the cytoplasmic membrane vi) two proteins which are responsible for synthesis of nucleotide activated D-GalA, i.e. Gla and Ugd. The UDP-D-GalA synthesis by Gla and Ugd from the housekeeping UDP-Glc was shown (Munoz R, Lopez R, de Frutos M, Garcia E: First molecular characterization of a uridine diphosphate galacturonate 4-epimerase: an enzyme required for capsular biosynthesis in *Streptococcus pneumoniae* type 1. Mol Microbiol 1999, 31(2):703-713)

vii) four proteins RmlACBD known to make TDP-L-Rhamnose. These genes are cryptic and probably dispensable for CPS production.

Taken together, this means that all necessary genes for making a type 1 CPS are encoded in the cluster, except:

a) biosynthetic genes encoding proteins for synthesis of the initiator sugar UDP-D-FucNAc4N;

b) a gene encoding a phosphorsugar transferase for adding the phospho-D-FucNAc4N to the lipid carrier Und-P. To synthesize the CPS type 1 by a modified LPS biosynthetic pathway it is necessary to provide a) and b) in an *E. coli* host strain in a way that by addition of the CPS type 1 cluster the pneumococcal LPS capsule can be synthetized. *E. coli* strains generally do not encode such enzymes. Remarkably, there is only a handful of microorganisms known that synthetize FucNAc4N and incorporate it into an polysaccharide: *S. pneumoniae* CP1 strains, *Shigella sonnei, Plesiomonas shigelloides* O17, and *Bacterioides fragilis*.

Figure 1:
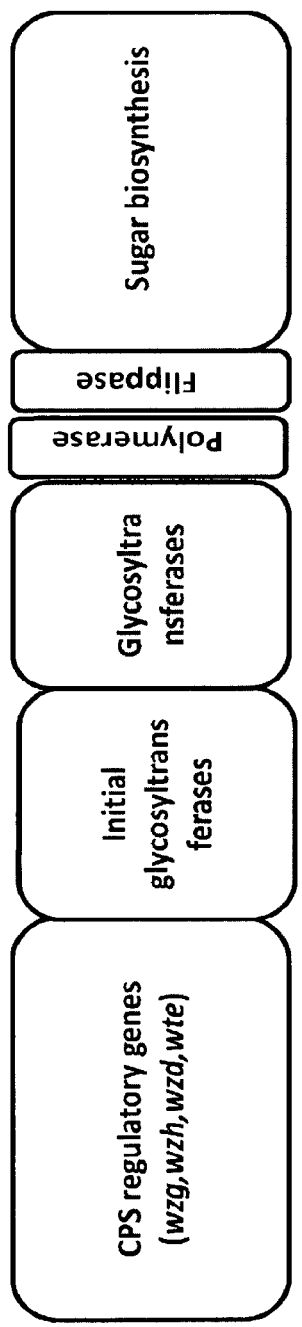
FIG. 1 Depicts the genetic organization of Capsular Polysaccharide Biosynthetic Pathway of S. pneumoniae. Schematic diagram of general genetic organization of capsular polysaccharide biosynthetic pathway of Streptococcus pneumoniae strains used for in vivo conjugation.
Figure 4:
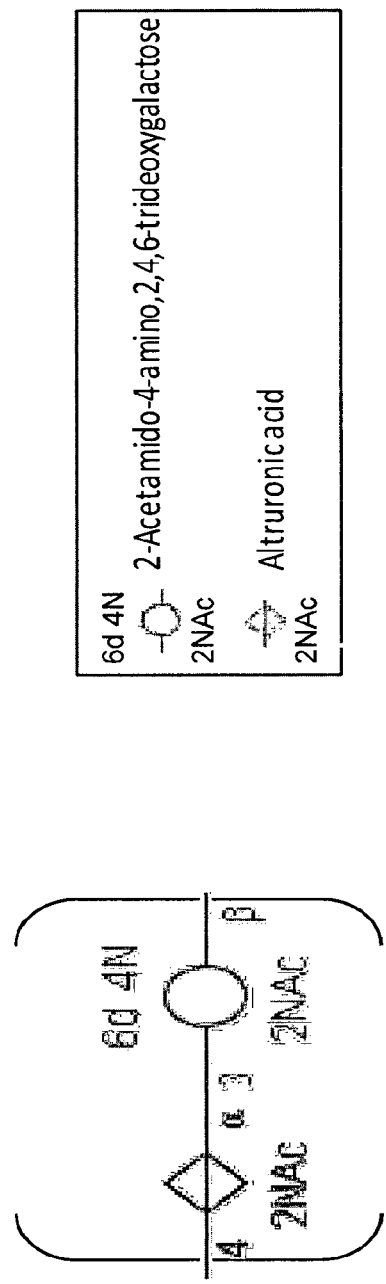
FIG. 4 Shows an O antigen subunit from S. sonnei and P. shigelloides. Schematic diagram of the S. sonnei and P. shigelloides repeat unit.
Figure 5:
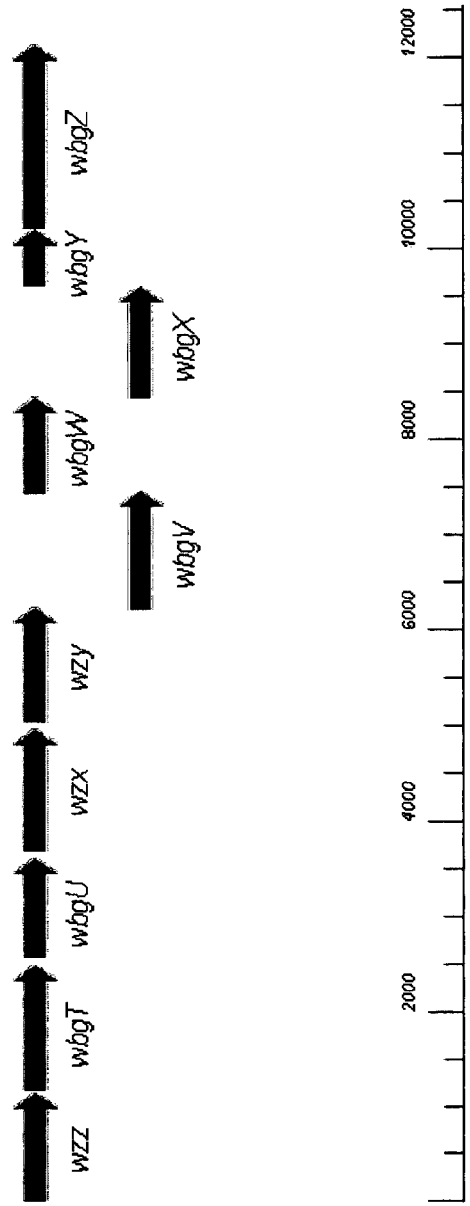
FIG. 5 Shows the P. shigelloides O17 antigen cluster. Plesiomonas shigelloides O17 O antigen cluster.

Thus we reasoned that it is necessary to find a gene cluster that provides the said functionalites. We achieved this by using genetic elements of the biosynthetic machinery for the synthesis of the *Shigella sonnei* or *Pseudomonas shigelloides* O17 O antigen. Both of these organisms synthetize an O antigen with identical structure. This O antigen is a genuine gram negative O antigen composed of a linear polymer composed of a disaccharide repeat unit -4-a-L-AltNAcA-1,3-a-D-FucNAc4N-1-, (FIG. 4) (Batta G, Liptak A, Schneerson R, Pozsgay V: Conformational stabilization of the altruronic acid residue in the O-specific polysaccharide of *Shigella sonnei/Plesiomonas shigelloides*. Carbohydr Res 1997, 305(1):93-99). The initiating sugar was shown to be D-FucNAc4N (Kubler-Kielb J, Vinogradov E, Ben-Menachem G, Pozsgay V, Robbins J B, Schneerson R: Saccharide/protein conjugate vaccines for *Bordetella* species: preparation of saccharide, development of new conjugation procedures, and physico-chemical and immunological characterization of the conjugates. Vaccine 2008, 26(29-30):3587-3593). The gene cluster required for biosynthesis (FIG. 5) is encoded in the genome of *P. shigelloides* and on a virulence plasmid in *S. sonnei* (Kopecko D J, Washington O, Formal S B: Genetic and physical evidence for plasmid control of *Shigella sonnei* form I cell surface antigen. Infection and immunity 1980, 29(1):207-214). The gene functions are putatively known by homology analysis (Xu D Q, Cisar J O, Ambulos Jr N, Jr., Burr D H, Kopecko D J: Molecular cloning and characterization of genes for *Shigella sonnei* form I O polysaccharide: proposed biosynthetic pathway and stable expression in a live salmonella vaccine vector. Infect Immun 2002, 70(8):4414-4423).

Thus, the strategy to assemble the biosynthetic machinery for CPS type 1 production in *E. coli* was as follows:

First, we aimed at reconstituting Und-PP-D-FucNAc4N production pathway. To achieve this, we recombinantly expressed the *P. shigelloides* O antigen cluster in *E. coli*.

Second, we deleted the L-AltNAcA glycosyltransferase from the *P. shigelloides* O17 cluster, resulting in an Und-PP-D-FucNAc4N truncated lipid precursor.

Third, we added the CPS type 1 cluster on a plasmid. Enzymes encoded in this plasmid were believed to extend the Und-PP-D-FucNAc4N precursor made by the *P. shigelloides* system to complete the CPS type 1 RU and polymerize the RUs to make a modified LPS.

Technically, this was done as follows:

In a first step, we cloned the *P. shigelloides* O antigen gene cluster (rfb*P. shigelloides*O17) into the donor plasmid pDOC-C (Lee D J, Bingle L E, Heurlier K, Pallen M J, Penn C W, Busby S J, Hobman J L: Gene doctoring: a method for recombineering in laboratory and pathogenic *Escherichia coli* strains. BMC Microbiol 2009, 9:252). By using this donor plasmid and a helper plasmid encoding a recombinase and an endonuclease (Kuhlman T E, Cox E C: Site-specific chromosomal integration of large synthetic constructs. Nucleic acids research 2010, 38(6):e92), we exchanged the rfb cluster of a W3110 ΔwecAwzzECA ΔwaaL *E. coli* strain by the *P. shigelloides* cluster (wzz to wbgZ, FIG. 5) from the plasmid by homologous recombination. See, e.g., International Application No. PCT/EP2013/071328, which is incorporated herein by reference in its entirety. The resulting chromosomally integrated strain makes recombinant O antigen which is reactive to the anti *S. sonnei* typing sera in western blotting.

The wbgW gene encoded within this integrated *P. shigelloides* cluster was deleted from the chromosome by homologous recombination according to the method of Datsenko and Wanner (Datsenko K A, Wanner B L: One-step inactivation of chromosomal genes in *Escherichia coli* K-12 using PCR products. *Proc Natl Acad Sci USA* 2000, 97(12):6640-6645). The resulting strain did not produce any anti *S. sonnei* specific lipid linked polysaccharide any longer, most likely due to the inability of the strain to make a complete disaccharide repeat unit.

Next, the CPS 1 cluster from wzg to ugd (FIG. 2) was cloned behind an artificial promoter (J23103, http://partsregistry.org/Part:BBa_J23103) and an optimal ribosomal binding site active in *E. coli.*

Expression of the described genetic system in a shake flask culture for analysis of lipid linked oligosaccharide biosynthesis generated a ladder like banding pattern in western blotting using an anti CPS type 1 specific antiserum (FIG. 6). This shows that the modified LPS biosynthesis pathway was collaborating in recombinant expression of CPS of the type 1 of *S. pneumoniae.*

To further provide evidence that the produced reactive, protease resistant material was indeed CPS type 1 linked to undecaprenyl pyrophosphate; an acid sensitivity test was applied to the samples from FIG. 6. Mild acid treatment by TFA abrogated the anti CPS type 1 signal, indicative for the presence of the pyrophosphate bond connecting polysaccharide and undecapenyl (FIG. 7). We found that it was possible to make a modified O antigen in the presence of the transporter genes wzg-wzd. To check if these genes had a direct effect, we deleted the four transporter genes from the CPS type 1 plasmid by homologous recombination (Bloor A E, Cranenburgh R M: An efficient method of selectable marker gene excision by Xer recombination for gene replacement in bacterial chromosomes. Applied and environmental microbiology 2006, 72(4):2520-2525). Coexpression of the modified plasmid surprisingly leads to loss of anti CPS type 1 signal (FIG. 8). This indicates that the transporter genes are required for efficient production of modified O antigen.

To show that the recombinant CPS type 1 can be used for glycosylation of proteins and thus the formation of protein-carbohydrate conjugates, we tested the bacterial protein glycosylation machinery (Wacker M, Linton D, Hitchen P G, Nita-Lazar M, Haslam S M, North S J, Panico M, Morris H R, Dell A, Wren B W et al: N-linked glycosylation in *Campylobacter jejuni* and its functional transfer into *E. coli. Science* 2002, 298(5599):1790-1793) for the ability of conjugate production in suitable recombinant *E. coli* strains.

An experiment was performed using the N-glycosylation system documented in (Feldman M F, Wacker M, Hernandez M, Hitchen P G, Marolda C L, Kowarik M, Morris H R, Dell A, Valvano M A, Aebi M: Engineering N-linked protein glycosylation with diverse O antigen lipopolysaccharide structures in *Escherichia coli*. Proc Natl Acad Sci USA 2005, 102(8):3016-3021; Kowarik M, Young N M, Numao S, Schulz B L, Hug I, Callewaert N, Mills D C, Watson D C, Hernandez M, Kelly J F et al: Definition of the bacterial N-glycosylation site consensus sequence. The EMBO journal 2006, 25(9):1957-1966; Wacker M, Linton D, Hitchen P G, Nita-Lazar M, Haslam S M, North S J, Panico M, Morris H R, Dell A, Wren B W et al: N-linked glycosylation in *Campylobacter jejuni* and its functional transfer into *E. coli*. Science 2002, 298(5599):1790-1793; Ihssen J, Kowarik M, Dilettoso S, Tanner C, Wacker M, Thony-Meyer L: Production of glycoprotein vaccines in *Escherichia coli*. Microbial cell factories 2010, 9:61.) The recombinant *E. coli* expressing the CPS type 1 lipid linked oligosaccharide was transformed with two inducible plasmids. One plasmid encoded the PglB enzyme, which is repeatedly shown to generally N glycosylate acceptor proteins (encoding a consensus amino acid sequence of the -D/E-x-N-x-S/T-type, in which x cannot be proline). On the second plasmid, the carrier protein EPA was encoded, which contains two inserted N glycosylation consensus sequences and a His-tag for Ni-affinity chromatography purification. After the glycosylation experiment, the EPA protein was purified and probed with anti his tag antisera (FIG. 9, panel A) and anti CPS type 1 antisera (FIG. 9, panel B) and clearly detected in elution fractions. This proves the PglB system in conjunction with the recombinant CPS type 1 expression system allows the efficient production of protein conjugates that can be used as anti-pneumococcal vaccine candidates.

Example 2: Synthesis of CPS4 Conjugates in *E. coli*

To further show that protein glycosylation can be used to produce active conjugates vaccines, we aimed at producing a CPS type 4 conjugate in the presence of the transporter genes as for CPS1.

CPS4 has a repeat unit structure containing a GalNAc at the reducing end (FIG. 10). The complete structure is:

-1,4-(2,3 S pyr)-a-D-Gal-1,3-a-D-ManNAc-1,3-a-L-FucNAc-1,3-a-D-GalNAc

Unlike the gene cluster of CPS1, the cluster encoding CPS type 4 from *S. pneumoniae* encodes all necessary enzymes to synthesize a CPS4 (FIG. 11). UDP-D-FucNAc and UDP-D-ManNAc are made by the proteins MnaA, FnlA, B, and C. The functions of different glycosyltransferases are predicted based on their homologies to other glycosyltransferases with known specificities. WciI is a predicted glycosylphosphate transferase and thus responsible for Und-PP-D-GalNAc synthesis, WciJ, K, and L are D-ManNAc, L-FucNAc, and D-Gal transferases, and WciM is a homolog of pyruvate transferases (Jiang S M, Wang L, Reeves P R: Molecular characterization of *Streptococcus pneumoniae* type 4, 6B, 8, and 18C capsular polysaccharide gene clusters. *Infect Immun* 2001, 69(3):1244-1255)

To reconstruct a CPS4 modified pathway in *E. coli*, we first cloned the CPS4 gene cluster (the genes between aliA and dexB) into a plasmid for expression in *E. coli* resulting in pGVXN803. In a second setup, we included only the genes downstream of the transporter genes (resulting in pGVXN753), i.e. wciJ-fnlC, to explicitly analyze the effects of wzg, wzh, wzd, and wze, as well as the effect of wciI deletion. WciI is a phosphor-sugar transferase homolog according to bioinformatics analysis. Similar activities are present in the *E. coli*, specifically the wecA gene encoded in the enterobacterial common antigen (ECA) cluster. In pGVXN753, we included an artificial promoter sequence upstream of the multiple cloning sites to ensure transcription of the inserted genes.

To analyze the effects of the above mentioned plasmids upon expression in *E. coli*, we transformed W3110 ΔwaaL cells with pGVXN753 and pGVXN803. W3110 ΔwaaL encodes the WecA protein that is responsible for the synthesis of Und-PP-D-GlcNAc, but is unable to make Und-PP-D-GalNAc. The latter lipid linked monosaccharide is the expected substrate for the enzymes of the CPS4 cluster which should complete the CPS4 RU. Thus, we provided in addition to a CPS4 cluster plasmid two different D-GlcNAc to D-GalNAc epimerases, Z3206 (Rush J S, Alaimo C, Robbiani R, Wacker M, Waechter C J: A novel epimerase that converts GlcNAc-P-P-undecaprenyl to GalNAc-P-P-undecaprenyl in *Escherichia coli* O157. *J Biol Chem* 2010, 285(3):1671-1680) and GalE (Linton D, Dorrell N, Hitchen P G, Amber S, Karlyshev A V, Morris H R, Dell A, Valvano M A, Aebi M, Wren B W: Functional analysis of the *Campylobacter jejuni* N-linked protein glycosylation pathway. Mol Microbiol 2005, 55(6):1695-1703). Both genes encode proteins that allow D-GalNAc synthesis in vivo, the former by epimerization of the lipid linked D-GlcNAc (Und-PP-D-GlcNAc<-> Und-PP-D-GalNAc), and the latter by using the nucleotide activated sugar as substrate (UDP-D-GlcNAc<->UDP-D-GalNAc).

FIG. 12 shows the results of the analysis. Cells were grown and epimerase expression was induced, and protease resistant biomass was separated by SDS-PAGE and analyzed by immunodetection after transfer of glycolipids to nitrocellulose membrane. The results show that whenever pGVXN803 was present in the cells, there was a ladder like signal detected by the anti CPS4 antiserum. pGVXN753 also induced a signal, albeit much weaker than the constructs that contained the transporter genes and wcil. Induction and nature of the epimerase did marginally influence signal strength. The strongest reactivity was obtained with pGVXN803 and the epimerase specific for the nucleotide activated sugar, suggesting that WciI is a D-GalNAc-phosphate transferase. Therefore surprisingly as for CPS1, the transporter genes are important for efficient production of CPS4 modified LPS in *E. coli*. To dissect the influence of the transporter genes versus the wcil, coexpression of wcil in presence of pGVX753 can be employed. Most likely, wcil alone is unable to enhance CPS4 expression to the level observed in presence of the transporter genes (i.e. in W3110 ΔwaaL containing pGVX803).

To further characterize the CPS4 produced in *E. coli*, we expressed pGVXN803 in *E. coli* SCM6 (Schwarz F, Huang W, Li C, Schulz B L, Lizak C, Palumbo A, Numao S, Neri D, Aebi M, Wang L X: A combined method for producing homogeneous glycoproteins with eukaryotic N-glycosylation. *Nat Chem Biol* 2010; SCM6 is deleted in wecA, ECA, waaL) and analyzed glycolipids by 2-AB labeling and MS/MS analysis. 2-AB labeling is a method which was developed to isolate, hydrolyze, modify poly- and oligosaccharides and analyze them by HPLC and MS/MS. Cells were grown overnight and were prepared and processed according to an established procedure (US2011/0274720).

Briefly, glycolipids were extracted from the biomass by organic solvents (Chloroform:Methanol:Water 10:10:3) and purified over C18 cartridges; eluates were treated with TFA in water/isopropanol to hydrolyze pyrophosphate bonds and release the glycan part from Und-PP-glycans. The resulting solution was passed over another C18 cartridge to remove lipids. The flow through was dried and the glycans were labeled with 2 aminobenzamide at the reducing end. The resulting labeled glycans were separated by HPLC using a gylcosepN normal phase column and detected by fluorescence (US2011/0274720 A1).

Resulting chromatograms are shown in FIG. 13 (panel A). Comparison of a chromatogram obtained from SCM6 cells containing or lacking pGVXN803 shows several peaks that are present in the former but lacking the latter. Some of these were analyzed by MS/MS for identification of the glycan identity and sequence. For several peaks it was possible to identify MS/MS patterns that are consistent with the expected CPS4 RU and polymer structures (indicated by arrows). Panel B of FIG. 13 shows the MALDI-MS/MS spectrum from the peak eluted at 53.8 minutes. Fragmentation ion series are consistent with the CPS4 RU modified with pyruvate at the non-reducing hexose.

We observed heterogeneity due to non-stoichiometric presence of pyruvate, indicative for either non quantitative modification of CPS4 repeat units with pyruvate or hydrolysis during sample preparation. We concluded from the data that we were able to generate a modified LPS biosynthetic pathway producing CPS4 glycans on Und-PP.

To further analyze the CSP4 glycolipids, we extracted glycolipids from *E. coli* SCM3 strain, (Faridmoayer A, Fentabil M A, Mills D C, Klassen J S, Feldman M F: Functional characterization of bacterial oligosaccharyltransferases involved in O-linked protein glycosylation. JOURNAL OF BACTERIOLOGY 2007, 189(22):8088-8098) expressing CSP4 and analyzed them as described above (FIG. 14) or directly used glycoplipids for in vitro glycosylation. In this experiment, glycolipids, an acceptor peptide containing the N glycosylation consensus sequence, and purified preparation of the oligosaccharyltransferase PglB are mixed (Jervis A J, Butler J A, Lawson A J, Langdon R, Wren B W, Linton D: Characterization of the structurally diverse N-linked glycans of *Campylobacter* species. JOURNAL OF BACTERIOLOGY 2012, 194(9):2355-2362). Glycopeptides are formed which can be analyzed by a HILIC chromatography followed (FIG. 15, panels A and B) by ESI-MS/MS for sequencing of the glycan. When the products from such an experiment were analyzed, exclusively pyruvylated glycans attached to peptides were identified (FIG. 15, panels C and D). Thus, the non-stoichiometric pyruvylation observed in FIGS. 13 and 14 most likely originated from hydrolysis of pyruvate from the glycan during sample preparation rather than non-quantitative decoration of the CPS4 RU. Thus, we claim that by the modified LPS biosynthesis pathway, it is possible to produce a CPS under native conditions allowing the synthesis of an active and possibly better conjugate compared to chemical conjugation.

Figure 16:
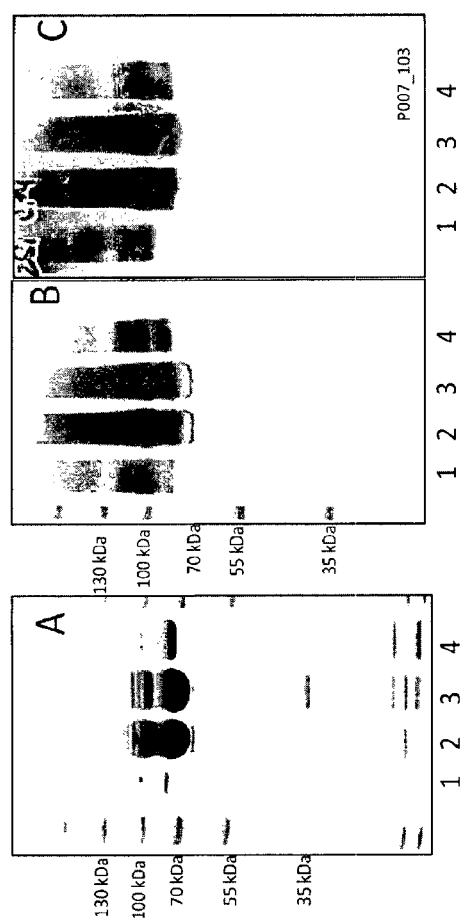

To test this hypothesis, we aimed at testing glycoconjugate in preclinical assays. In a first step, we used microbial fermentation to produce CPS4 conjugated to a generic carrier protein, genetically detoxified Exotoxin A of *Pseudomonas aeruginosa* (EPA, US2011/0274720 A1). *E. coli* W3110 ΔwaaL was transformed with pGVXN539 (expressing EPA carrier protein encoding 2 N glycosylation consensus sequences, (US2011/0274720 A1 and dyx), cloned in pACT3 (GenBank: U51556.1) in which the clmR cassette was replaced by a kanamycin resistance cassette (kanR); pGVXN114 (inducible expression of PglB, US2011/0274720 A1), pGVXN207 (inducible expression of GalE, (Rush J S, Alaimo C, Robbiani R, Wacker M, Waechter C J: A novel epimerase that converts GlcNAc-P-P-undecaprenyl to GalNAc-P-P-undecaprenyl in *Escherichia coli* O157. *J Biol Chem* 2010, 285(3):1671-1680) and pGVXN803 (encoding the CPS4 cluster). Cells were grown in TB medium and induced at suitable ODs and production was performed overnight. His tagged EPA was purified from periplasmic extracts prepared by the periplasmic extraction using lysozyme followed by IMAC. Analytical assays of elution fractions are shown in FIG. 16. SDS-PAGE and Coomassie staining show non- and glycosylated EPA at 70 and above 70 kDa, the latter being present in a ladder like pattern indicative for a (modified) O antigen glycan composed of RUs (FIG. 16, panel A). Immunodetection by anti His (FIG. 16, panel B) and anti CPS4 (FIG. 16, panel C) after electrotransfer to nitrocellulose membranes of the same fractions confirmed the presence of CPS4 and EPA in the material.

Glycoconjugates were further purified by anion exchange chromatography for separation of non- and glycosylated EPA; glycoprotein was then further purified by size exclusion chromatography. The resulting glycoprotein preparation was analyzed for monosaccharide composition using derivatization by 1-phenyl-3-methyl-5-pyrazolone (PMP, Lv L, Yang X, Zhao Y, Ruan Y, Yang Y, Wang Z: Separation and quantification of component monosaccharides of the tea polysaccharides from *Gynostemma pentaphyllum* by HPLC with indirect UV detection. *Food Chemistry* 2009, 112:742-746), which demonstrated that the glycan composition of recombinant glycoconjugate is identical to CPS4 isolated from *S. pneumoniae* (FIG. 17).

To test the vaccine activity of the glycoconjugates, immunization studies and opsonophagocytosis assays (OPA) were performed. OPA is a generally recognized assay to address the functionality of antibodies for eliminating *S. pneumoniae* cells and is a surrogate for protection. We immunized rabbits with different doses of EPA-CPS4 conjugate. As a control, we used Prevenar 13, a licensed and marketed product widely used for the prevention of pediatric pneumococcal disease. The resulting antisera were submitted to analysis by dot blot for immunogenicity (FIG. 18) and OPA for functionality according to a standardized protocol (Romero-Steiner S, Frasch C E, Carlone G, Fleck R A, Goldblatt D, Nahm M H: Use of opsonophagocytosis for serological evaluation of pneumococcal vaccines. *Clin Vaccine Immunol* 2006, 13(2):165-169).

Table 1 shows the relevant opsonic titers obtained. The results show that glycoconjugates recombinantly made in *E. coli* are equally well and in some instances even superior to the licensed vaccine comparator in terms of the ability to raise antisera active in the opsonophagocytotic assay.

Example 3: Synthesis of CPS14 Conjugates in *E. coli*

To further show that *E. coli* can be used for the production of CPS conjugates, we aimed at producing CPS14 conjugates. The CPS14 polysaccharide is encoded by CPS14 cluster (FIG. 19) in a similar architecture as CPS1 and CPS4. CPS14 consists of polymerized RUs with the following structure (FIG. 20): -1,6-(b-D-Gal-1,4)-b-D-GlcNAc-1,3-b-D-Gal-1,4-b-D-Glc-.

The biosynthesis of CPS14 starts with the addition of phospho-D-Glc to undecaprenyl phosphate (Und-P) by the activity of WchA. WchA was biochemically shown to be a phospho-glycose transferase, with identical activity as the *E. coli* WcaJ protein encoded by a gene in the colanic acid cluster. Further elongation of the D-Glc is achieved by the enzymatic actions of the other glycosyltransferases present in the cluster (Kolkman M A, van der Zeijst B A, Nuijten P J: Functional analysis of glycosyltransferases encoded by the capsular polysaccharide biosynthesis locus of *Streptococcus pneumoniae* serotype 14. *J Biol Chem* 1997, 272 (31):19502-19508). Detailed functions of the different ORFs in the CPS14 cluster are predicted for wzg, wzh, wzd, wze (regulator, and 3 transport associated genes), WchJK (D-Gal transferase), WchL (D-GlcNAc transferase), WchM (D-Gal transferase), Wzy (polymerase), Wzx (flippase). WciY is dispensable for CPS14 formation, whereas wchN deletion negatively influences CPS14 yields (Kolkman M A, Wakarchuk W, Nuijten P J, van der Zeijst B A: Capsular polysaccharide synthesis in *Streptococcus pneumoniae* serotype 14: molecular analysis of the complete cps locus and identification of genes encoding glycosyltransferases required for the biosynthesis of the tetrasaccharide subunit. *Mol Microbiol* 1997, 26(1):197-208). The CPS14 cluster is special in the sense that there are more functions encoded than minimally required for CPS14 biosynthesis. Most probably, some of the proteins with unassigned functions are auxiliary enzymes supporting biosynthesis of the capsule.

To test production of CPS14 polysaccharide in *E. coli* the CPS14 gene cluster consisting of the stretch from wchA to wciY was cloned into the pDOC donor plasmid (Lee D J, Bingle L E, Heurlier K, Pallen M J, Penn C W, Busby S J, Hobman J L: Gene doctoring: a method for recombineering in laboratory and pathogenic *Escherichia coli* strains. BMC Microbiol 2009, 9:252) designated for integration of CPS14 into O16 antigen cluster (pGVXN615) and transformed into *E. coli* strain GVXN1128 (W3110 ΔwaaL) Immunoblot analysis of the proteinase K digested *E. coli* cells harboring pGVXN615 showed a ladder-like pattern, which was detected with CPS14 antiserum that is used for capsular serotyping of clinical CPS14 isolates (Inset of FIG. 21, panel A). Furthermore, to accumulate a single repeating unit, the polymerase of CPS14 cluster, wzy, was deleted in pGVXN615 by transposon mutagenesis, resulting in pGVXN643. The glycolipids were extracted from *E. coli* cells transformed with pGVXN643 and analyzed by NP-HPLC after hydrolysis and fluorescent labeling as described above. A specific peak eluted at 57.4 minute (FIG. 21, panel A) from the glycosepN column MS and MS/MS analysis of this peak matched with expected mass and fragmentation pattern of a single repeating unit of CPS14 (FIG. 21, panel B). This confirms that expression of a partial CPS14 gene cluster under the control of an O antigen promoter can lead to a recombinant LPS biosynthetic CPS14 oligosaccharide production in a common *E. coli* host cell.

In order to improve and stabilize biosynthesis of CPS14 polysaccharide in *E. coli*, part of CPS14 cluster containing the stretch from wchA to wciY was cloned into the pDOC-C replacement plasmid (Lee D J, Bingle L E, Heurlier K, Pallen M J, Penn C W, Busby S J, Hobman J L: Gene doctoring: a method for recombineering in laboratory and pathogenic *Escherichia coli* strains. BMC Microbiol 2009, 9:252), designated for integration of CPS14 into *E. coli* colanic acid cluster (pGVXN710). Integration of CPS14 was completed in several *E. coli* strains, including GVXN1052 (W3110), GVXN1128 (W3110 ΔwaaL) and GVXN1716 (W3110 ΔwaaLΔwecA-wzzE) as described above. It has been shown that colanic acid genes are not expressed in *E. coli* under normal condition, and their expression is controlled by a complex network of regulators. It was identified that transcription of the colanic acid requires RcsA, a positive regulator (Ebel W, Trempy J E. J Bacteriol. 1999; 181(2):577-84). Immunoblot analysis of proteinase K digested *E. coli* strains in which the colanic acid cluster was replaced by the CPS14 cluster harboring a plasmid for expression of RcsA (pGVX688) showed a ladder-like pattern detected by CPS14 antiserum which was used for serotyping of clinical CPS14 isolates; this pattern was not detectable in the absence of RcsA (see FIG. 22). This result demonstrates that colanic acid is a sutitable target location to integrate polysaccharide biosynthetic pathways and that the expression of heterologous polysaccharide is tightly controlled by the *E. coli* RcsA protein.

To further characterize the CPS14 produced in E. coli, GVX6129 (W3110ΔwaaL CA::CPS14) was transformed into E. coli along with pGVXN688 (rcsA). Glycolipids were analyzed by 2-AB labeling and MS/MS analysis as described above. MS/MS analysis identified 2 and 3 subunits of CPS14, eluted at 95.9 min and 115.3, respectively (see FIG. 24).

To test the effect of expression of transporter genes on the production of CPS14 polysaccharide in E. coli, wzg to wze of the S. pneumoniae CPS14 cluster, containing the transporter genes was cloned into a low copy number plasmid with IPTG inducible promoter (pGVX 72) to form pGVX1497. The plasmid was transformed into E. coli strain GVX6126 (E. coli W3110 CA::CPS14), from which the wchA to wciY portion of the CPS14 cluster had been integrated into colanic acid E. coli. GVX6126 was transformed with pGVX72 or pGVX1497 and cultured, with induction of transporter gene expression using 0.01 mM IPTG. E. coli cells were harvested after over night incubation and digested with proteinase K, and a protease resistant biomass was separated by SDS-PAGE and analyzed by immunodetection after transfer of glycolipids to nitrocellulose membrane. The results show that in the presence of pGVXN1497 (expressing wzg-wzh-wzd-wze), a high molecular weight ladder like signal was detected by the anti CPS14 antiserum (see FIG. 23. Lane 3), and when pGVXN1497 was replaced with an empty vector (pGVX72), the ladder size was significantly reduced (see FIG. 23. Lane 2). This demonstrates a supporting requirement of transporter genes for the production of CPS.

The gtrABS operon is involved in the synthesis of glucose on Und-P, a cellular compound which is very similar to the native initiator step for CPS14 (synthetized by wchA), Und-PP. The gtrABS operon contains genes that encode enzymes involved in assembly of glucose on the Und-P in the cytoplasm, flipping of the glycolipid into the periplasm, and a glucosyltransferase which uses Und-P-glucose as a donor to transfer the glucose residue onto the reducing end GlcNAc of O16 subunit in the E. coli W3110.

To avoid production of two lipid precursors with D-Glc and to solely produce Und-PP-CPS14 and not Und-P-CPS14, an enzyme that only makes Und-PP-glucose as the initiator glucose can be used. In addition, the Und-P-glucose production pathway can be deleted. In this way, all CPS is linked to Und by a pyrophosphate linkage and thus available for glycosylation.

To further elucidate and optimize the biosynthetic pathway of CPS14 in E. coli, the initiator glucosyltransferase activity of the CPS14 pathway can be enhanced. This explored by deletion of wchA and wcaJ, and complementing them by plasmid borne overexpression strategies using the same genes and analysing the effects on glycolipid production.

A plasmid containing the wcaJ gene may well be transformed into E. coli strains containing CPS14 but lacking WchA and WcaJ (e.g. W3110 ΔwaaL ΔrfbO16::CPS14-clmR ΔwchA ΔgtrABS). Using established methods, the sugar production can be analysed in these strains. Based on these results, the optimum combination of genes for production of maximum amount of CPS14 linked to Und-PP could be determined and used to transform E. coli generating the optimal production strain. Certainly, this novel E. coli strain with superior sugar production could be ideal to enrich the production of glycosylated proteins, both N and O glycosylated. Moreover, this newly engineered strain could be used to generate different glycoconjugates, if additionally; diverse protein carriers are included in the production strain of any glycoconjugate containing Glc at the reducing end.

TABLE 1

'New Zealand White' rabbits were immunized on da y0, day 21 and day 42 with the indicated glycoconjugate vaccines (note, the stated amount in μg refers to the amount of polysaccharide/injection) via the sub-cutaneous route. The glycoconjugate vaccines were either adjuvanted with 0.12% $Al^{3+}$ for all three immunizations or with Freund's Complete Adjuvant (FCA) for the prime immunization (d0) and Freund's Incomplete Adjuvant (FIA) for the two boost immunizations (d21 and d42). Prevnar-13 was used according to the manufactures instructions and one human dose (corresponds to 2.2 μg CPS4 polysaccharide) was injected per immunization. Animals were sacrificed at day 56 and obtained serum was analysed for neutralizing activity in an opsonophagocytosis killing assay (OPK). The 'Opsonic Index' is defined as the dilution of serum that kills 50% of the bacteria (pneumococcal serotype 4).

| | | Opsonic Index | |
|---|---|---|---|
| Rabbit ID | Treatment | preimmune | postimmune |
| SZ 3415 | 2 μg CPS4-EPA/Alum | <8 | 2719 |
| SZ 3416 | | <8 | 777 |
| SZ 3417 | 10 μg CPS4-EPA/Alum | <8 | 1111 |
| SZ 3418 | | <8 | 2215 |
| SZ 3419 | 10 μg CPS4-EPA/FCA-FIA | <8 | 29068 |
| SZ 3420 | | <8 | 187543 |
| SZ 3421 | FCA-FIA only | <8 | <8 |
| SZ 3422 | | <8 | <8 |
| SZ 3423 | Prevnar-13 | <8 | 2753 |
| SZ 3424 | | <8 | 169 |

EQUIVALENTS

The methods, host cells, and compositions disclosed herein are not to be limited in scope by the specific embodiments described herein. Indeed, various modifications of the methods, host cells, and compositions in addition to those described will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

What is claimed is:

1. An engineered Gram-negative bacterium for the production of a recombinant glycoprotein, wherein the Gram-negative bacterium comprises (a) glycosyltransferases for producing a capsular polysaccharide of a gram positive bacterium (b) an oligosaccharyl transferase which is heterologous to the Gram-negative bacterium, and (c) nucleic acid encoding a carrier protein comprising a consensus sequence for glycosylation, wherein said Gram-negative bacterium is E. coli W3110, wherein genes encoding GtrA, GtrB and GtrS are partially or completely functionally inactivated or deleted from the Gram-negative bacterium.

2. The Gram-negative bacterium of claim 1 wherein the functional inactivation of the gene encoding the GtrA, GtrB and GtrS enzyme results in elimination of Und-P linked glucose.

3. The Gram-negative bacterium of claim 1 wherein the gene encoding the GtrA, GtrB and GtrS enzyme of the Gram-negative bacterium is deleted.

4. The Gram-negative bacterium of claim 1 wherein the genes encoding the GtrA, GtrB and GtrS are functionally inactivated.

5. The Gram-negative bacterium of claim 4 wherein the genes encoding the GtrA, GtrB and GtrS are deleted.

6. The Gram-negative bacterium of claim 1, wherein the Gram-negative bacterium comprises a regulatory gene of a capsular polysaccharide gene cluster of *Streptococcus pneumoniae*, wherein the gene encoding the GtrA, GtrB and GtrS enzyme of the Gram-negative bacterium is functionally inactivated.

7. The Gram-negative bacterium of claim 6 wherein the gene encoding the GtrA, GtrB and GtrS enzyme of the Gram-negative bacterium is deleted.

8. The Gram-negative bacterium of claim 6 wherein the genes encoding GtrA, GtrB and GtrS are functionally inactivated.

9. The Gram-negative bacterium of claim 8 wherein the genes encoding GtrA, GtrB and GtrS are deleted.

10. The Gram-negative bacterium of claim 1, wherein the nucleic acid encoding the carrier protein is heterologous to the Gram-negative bacterium.

11. The Gram-negative bacterium of claim 1, wherein said carrier protein is detoxified exotoxin A from *P. aeurginosa*.

12. The Gram-negative bacterium of claim 1, wherein said carrier protein is conjugated to the polysaccharide by the oligosaccharyl transferase.

13. The Gram-negative bacterium of claim 1 wherein the polysaccharide is a capsular polysaccharide of *Streptococcus pneumoniae*.

14. A recombinant glycoprotein produced by the Gram-negative bacterium of claim 1.

15. A method of producing a recombinant glycoprotein comprising culturing the Gram-negative bacterium of claim 1 under conditions suitable for the production of proteins.

16. The method of claim 15 further comprising purifying the recombinant glycoprotein.

* * * * *